US006676600B1

(12) United States Patent
Conero et al.

(10) Patent No.: US 6,676,600 B1
(45) Date of Patent: Jan. 13, 2004

(54) SMART PHYSIOLOGIC PARAMETER SENSOR AND METHOD

(75) Inventors: Ronald S. Conero, San Diego, CA (US); Stuart L. Gallant, San Diego, CA (US)

(73) Assignee: Tensys Medical, Inc., San Diego, CA (US)

( * ) Notice: Subject to any disclaimer, the term of this patent is extended or adjusted under 35 U.S.C. 154(b) by 470 days.

(21) Appl. No.: 09/652,626

(22) Filed: Aug. 31, 2000

Related U.S. Application Data

(60) Provisional application No. 60/152,534, filed on Sep. 3, 1999.

(51) Int. Cl.[7] .................................................. A61B 8/06
(52) U.S. Cl. ........................ 600/438; 600/491; 73/1.57
(58) Field of Search ........................ 439/620; 600/437, 600/459, 454–456, 485–488, 491; 73/1.57

(56) References Cited

U.S. PATENT DOCUMENTS

| | | | |
|---|---|---|---|
| 3,724,274 A | * | 4/1973 | Millar ............................ 338/4 |
| 4,608,994 A | | 9/1986 | Ozawa et al. |
| 4,688,579 A | | 8/1987 | Inahara |
| 4,695,955 A | | 9/1987 | Faisandier |
| 4,754,401 A | | 6/1988 | Kaczynski et al. |
| 4,889,132 A | | 12/1989 | Hutcheson et al. |
| 4,995,399 A | | 2/1991 | Hayashi et al. |
| 5,012,411 A | | 4/1991 | Policastro et al. |
| 5,050,613 A | | 9/1991 | Newman et al. |
| 5,072,733 A | | 12/1991 | Spector et al. |
| 5,158,091 A | | 10/1992 | Butterfield et al. |
| 5,251,631 A | * | 10/1993 | Tsuchiko et al. ............ 600/447 |
| 5,437,284 A | * | 8/1995 | Trimble |
| 5,479,096 A | * | 12/1995 | Szczyrbak et al. ........... 324/132 |
| 5,606,977 A | | 3/1997 | Ramsey et al. |
| 5,617,857 A | | 4/1997 | Chader et al. |
| 5,649,543 A | | 7/1997 | Hosaka et al. |
| 5,699,807 A | | 12/1997 | Motogi et al. |
| 5,709,212 A | | 1/1998 | Sugo et al. |
| 5,720,293 A | | 2/1998 | Quinn et al. |
| 5,735,799 A | | 4/1998 | Baba et al. |
| 5,749,361 A | | 5/1998 | Mateyko |
| 5,857,967 A | | 1/1999 | Frid et al. |
| 5,868,679 A | | 2/1999 | Miyazaki |
| 5,873,834 A | | 2/1999 | Yanagi et al. |
| 5,876,347 A | | 3/1999 | Chesney et al. |
| 5,916,180 A | | 6/1999 | Cundari et al. |
| 5,921,936 A | | 7/1999 | Inukai et al. |
| 6,032,109 A | * | 2/2000 | Ritmiller, III ............... 702/104 |
| 6,298,255 B1 | * | 10/2001 | Cordero et al. ............. 600/372 |

FOREIGN PATENT DOCUMENTS

| | | |
|---|---|---|
| EP | 0 342 249 A1 | 5/1988 |
| WO | WO 92/07508 | 10/1991 |
| WO | WO 97/29678 | 2/1997 |

\* cited by examiner

Primary Examiner—Francis J. Jaworski
(74) Attorney, Agent, or Firm—Gazdzinski & Associates

(57) ABSTRACT

A sensor assembly used for the measurement of one or more physiologic parameters of a living subject which is capable of storing both data obtained dynamically during use as well as that programmed into the device. In one embodiment, the sensor assembly comprises a disposable combined pressure and ultrasonic transducer incorporating an electrically erasable programmable read-only memory (EEPROM), the assembly being used for the non-invasive measurement of arterial blood pressure. The sensor EEPROM has a variety of information relating to the manufacture, run time, calibration, and operation of the sensor, as well as application specific data such as patient or health care facility identification. Portions of the data are encrypted to prevent tampering. In a second embodiment, one or more additional storage devices (EEPROMs) are included within the host system to permit the storage of data relating to the system and a variety of different sensors used therewith. In a third embodiment, one or more of the individual transducer elements within the assembly are made separable and disposable, thereby allowing for the replacement of certain selected components which may degrade or become contaminated. Methods for calibrating and operating the disposable sensor assembly in conjunction with its host system are also disclosed.

21 Claims, 14 Drawing Sheets

SMART PHYSIOLOGIC PARAMETER SENSOR AND METHOD

Pursuant to 35 U.S.C. 119(e), this application claims priority benefit of U.S. provisional patent application Ser. No. 60/152,534 entitled "Smart Blood Pressure Sensor and Method" filed Sep. 3, 1999.

BACKGROUND OF THE INVENTION

1. Field of the Invention

The present invention relates to the field of medical instrumentation, specifically the use of electronic storage devices for storing and retrieving data relating to, inter alia, particular instruments or patients.

2. Description of Related Technology

The ability to readily measure various physiologic parameters associated with a living subject, such as arterial blood pressure or ECG, is often critical to providing effective care to such subjects. Typically, under the prior art, measurement of such parameters is accomplished using a system comprising a host device such as a portable or semi-portable monitoring station that is used in conjunction with a replaceable/disposable probe or sensor assembly, the latter being in direct contact with the subject and measuring the physical parameter (or related parameters) of interest. Such replaceable and disposable sensor assemblies are highly desirable from the standpoint that the risk of transfer of bacterial or other contamination from one patient to the next is significantly mitigated; the portion of the sensor assembly (or for that matter entire assembly) in contact with a given subject is replaced before use on another subject.

However, despite the mitigated risk of contamination, the use of such prior art disposable sensors also includes certain risks. One such risk relates to the potential re- use of what are meant to be single-use only components. Inherently, individuals or health care providers may attempt to re-use such single use components if there is no seeming degradation of the component or perceived threat of contamination. However, in the case of certain devices, the degradation of the component may be insidious and not immediately perceptible to the user. For example, the offset (i.e., difference of voltage generated by the device at certain prescribed conditions) associated with an elastomer-coated pressure transducer used in a non-invasive blood pressure monitoring device may change progressively in small increments over time due to swelling of the elastomer coating resulting from exposure to certain chemical substances. This variation in offset manifests itself as a change in the ultimate blood pressure reading obtained using the device, thereby reducing its accuracy. Hence, the readings obtained using the instrument may appear to be reasonable or correct, but in fact will incorporate increasing amounts of error from the true value of the parameter, which may significantly impact the treatment ultimately provided to the subject. Hence, what is needed is an approach wherein any such degradable or single use components are reliably replaced at the necessary interval such that performance does not appreciably degrade.

A related issue concerns the re-use of such devices on different patients. Specifically, if the "single use" components are perceived by the user not to degrade rapidly, the user may be tempted to use the device (including the single use transducer(s)) on several different patients. Aside from the aforementioned performance issues, such repeated use may be hazardous from a contamination standpoint, as previously discussed. Ideally, portions of the device capable of transmitting bacterial, viral, or other deleterious agents are disposed of and replaced prior to use on another patient.

Another risk concerns the use of third party or non-compliant sensors with the host device of the original equipment manufacturer (OEM). While such third party sensors may ostensibly be manufactured to the design specifications and requirements of the OEM, in many cases they are not, which can result in readings obtained using the system which are less than accurate or even wholly non-representative of the parameter being measured. Even OEM supplied disposable sensors may have defects. Another troubling aspect is the fact that the caregiver or health care professional who is provided with such disposable sensors may have no means by which to verify the quality or acceptability of a given replaceable sensor, and therefore the accuracy of any reading they may obtain using that sensor may be called into question. Hence, even if the majority of sensors within a given lot obtained from the third party manufacturer are acceptable in terms of performance, the caregiver often has no way of knowing whether the next replacement sensor they use will perform as designed or intended by the OEM and yield representative results. In the ideal case, the quality of each individual replacement sensor would be determined by the host system prior to use (such as when the new replacement sensor is first installed on the host), and the caregiver apprised of the results of this determination.

The calibration of the replaceable/disposable sensor, whether OEM or otherwise, and the host system must also be considered. Under the prior art approach, calibration is most often performed on the system as a whole at a discrete point in time, and is generally not performed before each use of the device after a new sensor or probe has been installed. Hence, the calibration of the host system and replaceable sensor as a whole is not specific to each given sensor, but rather to a "nominal" sensor (i.e., the one in place in the system when the calibration was performed). For example, the system may be calibrated before first use, and then periodically thereafter at predetermined intervals, or at the occurrence of a given condition. Under this approach, changes in the physical operating characteristics of the host system may result in changes in the calibration over time. Due to any number of intrinsic or external factors, the device may "drift" between calibrations, such that a reading taken with the device immediately following calibration may be substantially different from that obtained using the same device and identical conditions immediately before the next calibration.

Additionally, due to manufacturing tolerances and variations, the performance of each individual replaceable sensor may vary significantly from other similar devices, as previously described. Such variations are generally accounted for by the OEM by specifying a maximum allowable tolerances or variances for certain critical parameters associated with the sensors; if these tolerances/variances are met for a given replaceable sensor, then the accuracy of the system as a whole will fall within a certain (acceptable) tolerance as well. Ideally, however, the system would be calibrated specifically to each individual replaceable sensor immediately prior to use, a capability which is not present in prior art disposable medical devices.

Another concern relates to the potential for surreptitious alteration of data stored by an instrument prior to or during operation. As with many other types of devices, the ability to make a device "tamperproof" is of significant importance, in that this provides the caregiver and subject with additional assurance that the disposable sensor in use is the correct type of sensor for the host system, that the sensor assembly and host system are properly calibrated, and that the disposable sensor has not been used on other subjects.

Lastly, it is recognized that prior art measurement systems do not include the facility for evaluating the accuracy of a given measurement or host/sensor combination after readings have been taken. Many systems are capable of storing data relating to a measurement obtained from a subject in terms of the estimated value(s) derived by the system, yet none of which the Assignee hereof is aware allow for the retrieval of data specific to a given sensor or permit the system operator to evaluate the performance (and accuracy) of the system historically. Such information is of great potential utility in the medical field, especially with relation to medical malpractice litigation, by enabling the caregiver or OEM to reconstruct the operation of their equipment to demonstrate that a given measurement obtained using a given sensor and host unit was in fact accurate, that the disposable sensor had been replaced prior to use on the patient, and the like. The availability of this information may also produce the added benefit of reduced medical malpractice insurance premiums for facilities using such systems, since the potential for fraudulent claims relating to the system is reduced.

Based on the foregoing, what is needed is an apparatus and associated method useful for measuring one or more physiologic parameters associated with a living subject wherein any degradable or single use components associated with the apparatus may be easily and reliably replaced so as to ensure that (i) the accuracy of the system and any measurements resulting there from do not degrade; (ii) cross-contamination between subjects does not occur; and (iii) the operating history of the replaced components and system as a whole may be subsequently retrieved for analysis.

SUMMARY OF THE INVENTION

The present invention satisfies the aforementioned needs by an improved apparatus and method for monitoring the physiologic parameters, such as for example arterial blood pressure, of a living subject.

In a first aspect of the invention, an improved sensor assembly incorporating an electronic storage element is disclosed. In a first embodiment, the device comprises one or more ultrasonic transducers and a removable (and disposable) pressure transducer, the latter further including a storage device in the form of an electrically erasable programmable read-only memory (EEPROM) capable of storing data and information relating to the operation of the sensor assembly, host system, and patient. The sensor EEPROM includes a variety of information relating to the manufacture, run time, calibration, and operation of the pressure transducer, as well as application specific data such as patient or health care facility identification. Portions of the data are encrypted to prevent tampering. Furthermore, the host system is programmed such that the sensor assembly will be rejected and rendered unusable by the host if certain portions of the aforementioned data do not meet specific criteria. In this fashion, system operational integrity, maintainability, and patient safety are significantly enhanced. In a second embodiment, one or more additional storage devices (e.g., EEPROMs) are included within the host system to permit the storage of data relating to the system and a variety of different sensors used therewith. In a third embodiment, a single storage device (e.g., EEPROM) is associated with the entire sensor assembly, including ultrasonic transducer(s) and pressure transducer, and adapted to store and provide data relating thereto.

In a second aspect of the invention, an improved sensor housing assembly is disclosed. In one exemplary embodiment, the housing assembly comprises first and second housing elements which are fabricated from a low cost polymer and which include recesses containing the ultrasonic and pressure transducer elements, respectively. The first housing element is adapted to removably receive the second such that the active faces of the ultrasonic and pressure transducer elements are substantially aligned when the housing elements are assembled, and the second housing element (and associated pressure transducer with EEPROM) can be readily disposed of and replaced by the user when required without having to replace or dislocate the first housing element. In a second embodiment, the first housing element is also made optionally removable from the sensor assembly such that the user may optionally replace just the pressure transducer/EEPROM, the ultrasonic transducer(s), or both as desired.

In a third aspect of the invention, an improved system for measuring one or more physiologic parameters of a living subject is disclosed. In one embodiment, the physiologic parameter measured comprises arterial blood pressure in the radial artery of a human being, and the system comprises the aforementioned sensor assembly having at least one ultrasonic transducer capable of generating and receiving ultrasonic signals, a pressure transducer capable of measuring the pressure applied to its active surface, and a storage device associated therewith; a local controller assembly in data communication with the sensor assembly further including an applanation/lateral device and controller, and a remote analysis and display unit having a display, signal processor, and storage device in data communication with the local controller assembly. Calibration and other data pertinent to the sensor assembly which is stored in the storage device (e.g., EEPROM) of the sensor assembly is read out of the EEPROM and communicated to the analysis and display unit, wherein the processor within the unit analyzes the data according to one or more algorithms operating thereon. Signal processing circuits present within the local controller assembly are also used to analyze electrical signals and data relating to the operation of the sensor assembly.

In a fourth aspect of the invention, an improved circuit used in effectuating the calibration of the transducer element (s) of the aforementioned sensor array are disclosed. In one exemplary embodiment, the circuit comprises an analog circuit having a transducer element, a span TC compensation resistor $R_a$, analog-to-digital converter (ADC), digital-to-analog converter (DAC), and operational amplifiers. The voltage output of the pressure transducer (bridge) is input to a first stage instrumentation amplifier which amplifies the transducer output signal. The amplified output is input to a second stage amplifier, along with the output of the DAC, which is subtracted from the signal. The output of the second stage amplifier represents the temperature compensated, zero offset output signal of the circuit. The DAC converts a digital signal derived from the system processor to compensate the output for the offset of the bridge, as well as the temperature coefficient of the offset. The ADC is used to measure the bridge voltage, which varies with temperature by virtue of span compensation resistor Ra. Resistor Ra has a near zero TC, while the bridge itself has a positive TC. Thus, the bridge voltage varies with temperature, and can be correlated to the offset variation with temperature. In a second embodiment, the DAC and second amplifier are omitted, and replaced by a high resolution ADC. The converter must have the dynamic range and signal to noise ratio to measure the large output swing from the instrumentation amplifier. This is true, because the output now contains both the signal, and the offset error, and offset TC error. In this embodiment, the bridge voltage still varies with temperature and is digitized by the ADC after amplification, but all the compensation is handled by digital signal processing in the system processor.

In a fifth aspect of the invention, an improved method of operating a disposable sensor in conjunction with its host system is disclosed. In one embodiment, the method comprises storing at least one data field within the aforementioned storage device of the sensor, connecting the sensor to a host system, and determining the compatibility of the sensor with the host device based at least in part on the at least one data field. In a second embodiment of the method, the sensor is operated in order to obtain data from at least one living subject; this data is then stored within the sensor and/or host system in order to provide a retrievable record of the operation of the sensor and of the specific patient tested.

In a sixth aspect of the invention, an improved method of calibrating a transducer element used within a blood pressure monitoring device is disclosed. The method comprises providing a transducer element having a predetermined operating response and associated storage device; determining the operating response for the transducer; determining a plurality of calibration parameters based on the determined operating response; storing data representative of the calibration parameters within the storage device; and calibrating the transducer during operation based at least in part on the stored calibration parameters. In one embodiment, the transducer element comprises a silicon strain beam pressure transducer and the calibration parameters comprise reference voltage and temperature values, linearity, sensitivity, and shunted resistor values calculated using a series of predetermined functional relationships. These calibration parameters are stored in the EEPROM previously described at time of manufacture. When used during normal operation, the output of the pressure transducer is calibrated by the host system using the pre-stored calibration parameters taken directly from the EEPROM during each individual use.

In a seventh aspect of the invention, an improved method of ensuring the condition of limited (e.g., single) use components within a blood pressure monitoring device is disclosed. The method generally comprises providing a blood pressure monitoring device including a removable sensor assembly; measuring at least one parameter of a living subject using the device and sensor assembly to obtain first data; storing the first data relating to the at least one parameter; measuring the at least one parameter at a second time to obtain second data; comparing the stored first data to the second data using a predetermined criterion; and disabling the blood pressure measuring device if the criterion is not satisfied. In one embodiment, the sensor assembly comprises a pressure transducer and one or more ultrasonic transducers, which are collectively used to gather parametric data relating to the blood pressure within the radial artery of the subject. The parametric data is stored within the EEPROM, and compared with subsequent measurements taken with the same device using a comparison algorithm. In this fashion, significant differences between the parametric data obtained in successive readings is detected, which indicates that the caregiver has used the device on different patients. If certain acceptance criteria are exceeded, the system generates a disable signal which prevents completion of the analysis and display of the current measurement, as well as any subsequent measurements, until the pressure transducer (and optionally ultrasonic transducers) is/are replaced.

DETAILED DESCRIPTION OF THE PREFERRED EMBODIMENT

Reference is now made to the drawings, in which like numerals refer to like parts throughout. For purposes of clarity, the following description of the subject invention is cast in the context of arterial blood pressure measuring systems utilizing the principle of arterial tonometry and ultrasonic wave analysis. Such blood pressure monitoring systems are disclosed, for example, in co-pending U.S. patent application Ser. No. 09/342,549, entitled "Method and Apparatus for the Non-Invasive Determination of Arterial Blood Pressure", filed Jun. 29, 1999, which is assigned to the assignee hereof, and incorporated herein by reference in its entirety. Alternatively, the methods and apparatus described in co-pending U.S. patent application Ser. No. 09/534,900 entitled "Method and Apparatus for Assessing Hemodynamic Parameters Within the Circulatory System of a Living Subject" filed Mar. 23, 2000, also incorporated herein by reference in its entirety, may be used in conjunction with the present invention. Other methods and apparatus, regardless of theory or principles of operation, may also be substituted.

It is also noted that while the invention is described herein in terms of a method and apparatus for assessing the hemodynamic parameters of the circulatory system via the radial artery (i.e., wrist) of a human subject, the invention may also be embodied or adapted to monitor such parameters at other locations on the human body, as well as monitoring these parameters on other warm-blooded species. All such adaptations and alternate embodiments are considered to fall within the scope of the claims appended hereto.

The present invention generally comprises a "smart" blood pressure sensor assembly which is used in conjunction with blood pressure system and host device in order to provide the enhanced functionality of the invention. This functionality includes, inter alia, (i) the ability to pre-store data relating to the manufacture, configuration, and calibration of the sensor assembly prior to use; (ii) the ability to use the pre-stored data to calibrate and enable/disable the sensor assembly during use, based on certain parameters and analyses conducted when the sensor assembly is connected to the host device; and (iii) the ability to store data obtained by the sensors or designated by the subject or caregiver within the sensor assembly and/or the host device during use. Each of these aspects in one fashion or another enhances the accuracy and reliability of blood pressure measurements taken with the system, as described in greater detail in the following paragraphs.

Sensor Assembly and Housing

Figure 1B:
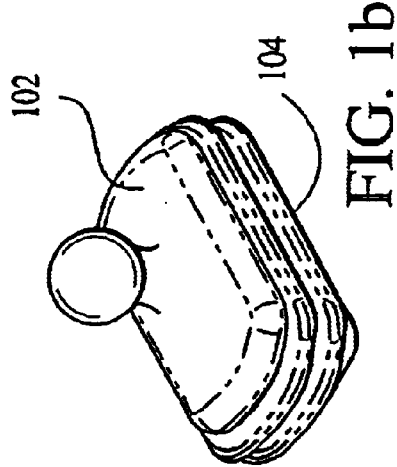
FIG. 1b is top perspective view of the sensor assembly of FIG. 1, shown assembled.
Figure 1C:
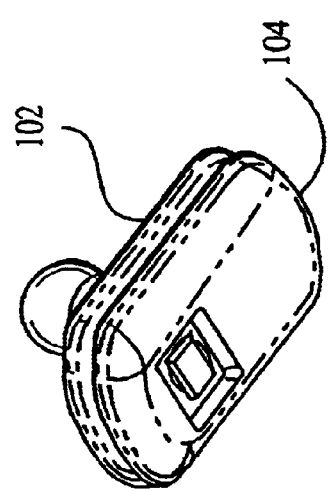
FIG. 1c is bottom perspective view of the sensor assembly of FIG. 1, shown assembled.
Figure 1A:
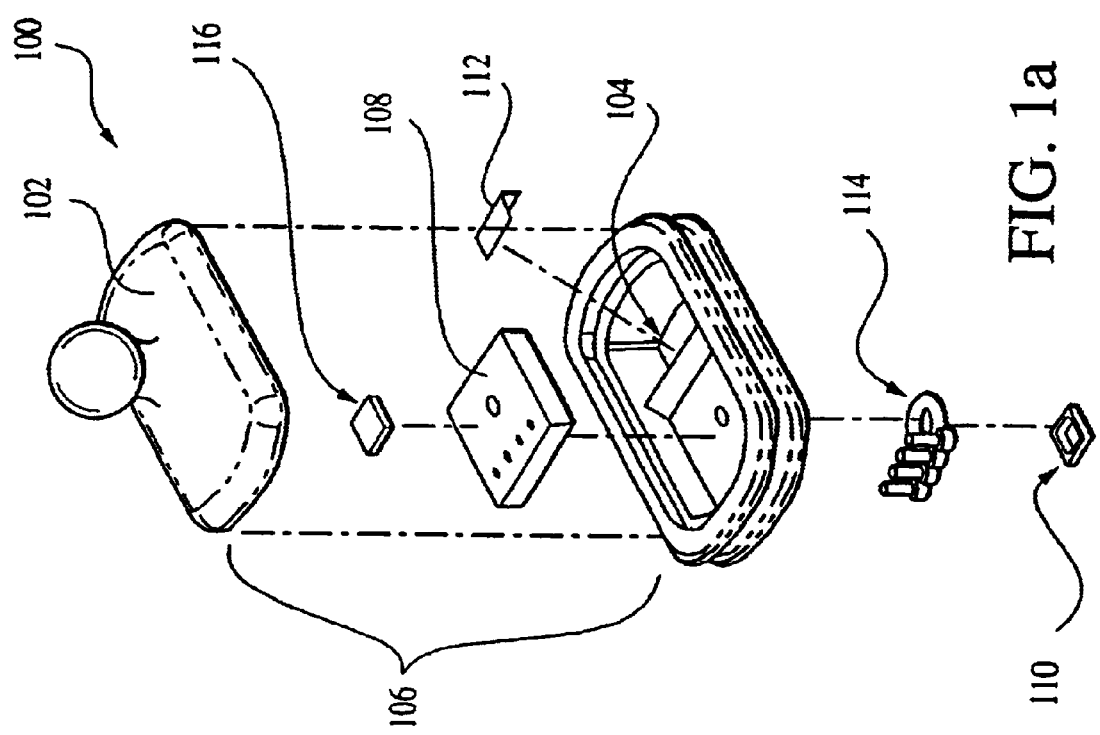
FIG. 1a is an exploded perspective view of a first embodiment of the smart sensor assembly according to the present invention.

Referring now to FIGS. 1a–1c, a first embodiment of the smart sensor assembly 100 of the present invention is described. As shown in FIGS. 1a–1c, the sensor assembly 100 of this embodiment comprises a cover 102 and main sensor housing 104 which are mated together to form the sensor body 106. The shape of the cover 102 and sensor housing 104 is generally that of an elongate rectangle, although it will be recognized that other shapes may be used. A mounting element 107 is formed in the cover 102 to permit, inter alia, positional control of the assembly 100 by the local controller assembly 444 (FIG. 4), as well as an electrical penetration (not shown) for providing power for and data communication with the assembly 100. In the illustrated embodiment, the mounting element is generally spherical or ball-shaped to permit the assembly to couple to the applanation mechanism 407 and operate in a variety of orientations with respect to the local controller 444, although other arrangements (such as universal joints, Heim joints, etc.) well known in the mechanical arts may be used.

The housing 104 and cover 102 of the illustrated embodiment are fabricated from a high strength, low cost polymer such as polycarbonate to provide the desired mechanical and electrical properties while still making the disposal of the assembly 100 economically feasible. Other materials (both polymeric and not) may be substituted depending on the properties and attributes desired.

The main housing 104 and cover 102 enclose a number of components, including a printed circuit board (PCB) 108, sensors in the form of a pressure transducer chip 110 and ultrasonic transducer (e.g., PZT) 112, bonding ring 114 for the pressure transducer chip 110, and storage device 116. In the embodiment of FIGS. 1a–1c, the storage device 116 and pressure and ultrasonic transducers 110, 112 are mounted onto the PCB 108 in a manner well understood to those of ordinary skill in the electrical arts, although other arrangements may be used. The storage device 116 of the embodiment of FIGS. 1a–1c is an electrically erasable programmable read only memory (EEPROM), although it will be appreciated that other types of storage devices such as an erasable PROM (EPROM), ultraviolet EPROM (UVEPROM), SRAM, DRAM, SDRAM, flash memory, or magnetic media may conceivably be used for a portion or all of the desired functionality. The storage device 116 chosen for use in the present embodiment is a 1K EEPROM device manufactured by Microchip Corporation, which operates from a 5 volt supply and utilizes a 2 wire serial link for data transfer. The 1K byte EEPROM is small in size and packaged in a SOT-23 package. This device 116 allows for cost-effective non-volatile storage of up to 1024 bits of information organized as 128 8-bit words. In the illustrated configuration, the entire device may be written in a time period on the order of one second, thereby providing rapid storage capability. The device also nominally allows 1 million write cycles, thereby allowing for extended use within a given sensor. Data retention of the device is on the order of 100 years, thereby greatly exceeding the anticipated shelf life of the assembly 100 as a whole.

The aforementioned EEPROM is easily accommodated within the sensor housing 104 on the PCB 108. Connections are made in the present embodiment by wire bonding or alternate methods at the same time the pressure transducer is connected 110, although other assembly and bonding methods may be used. A gel cup (not shown) or other means may optionally be used to protect the EEPROM 116 from electrostatic discharge or other electrical or physical trauma. Electrical signals are transferred in and out of the sensor assembly 100 using a plurality of electrical conductors (not shown) of the type well known in the art. Essentially any configuration of electrical connector or coupling may be substituted depending on the needs of the particular application.

Figure 2A:
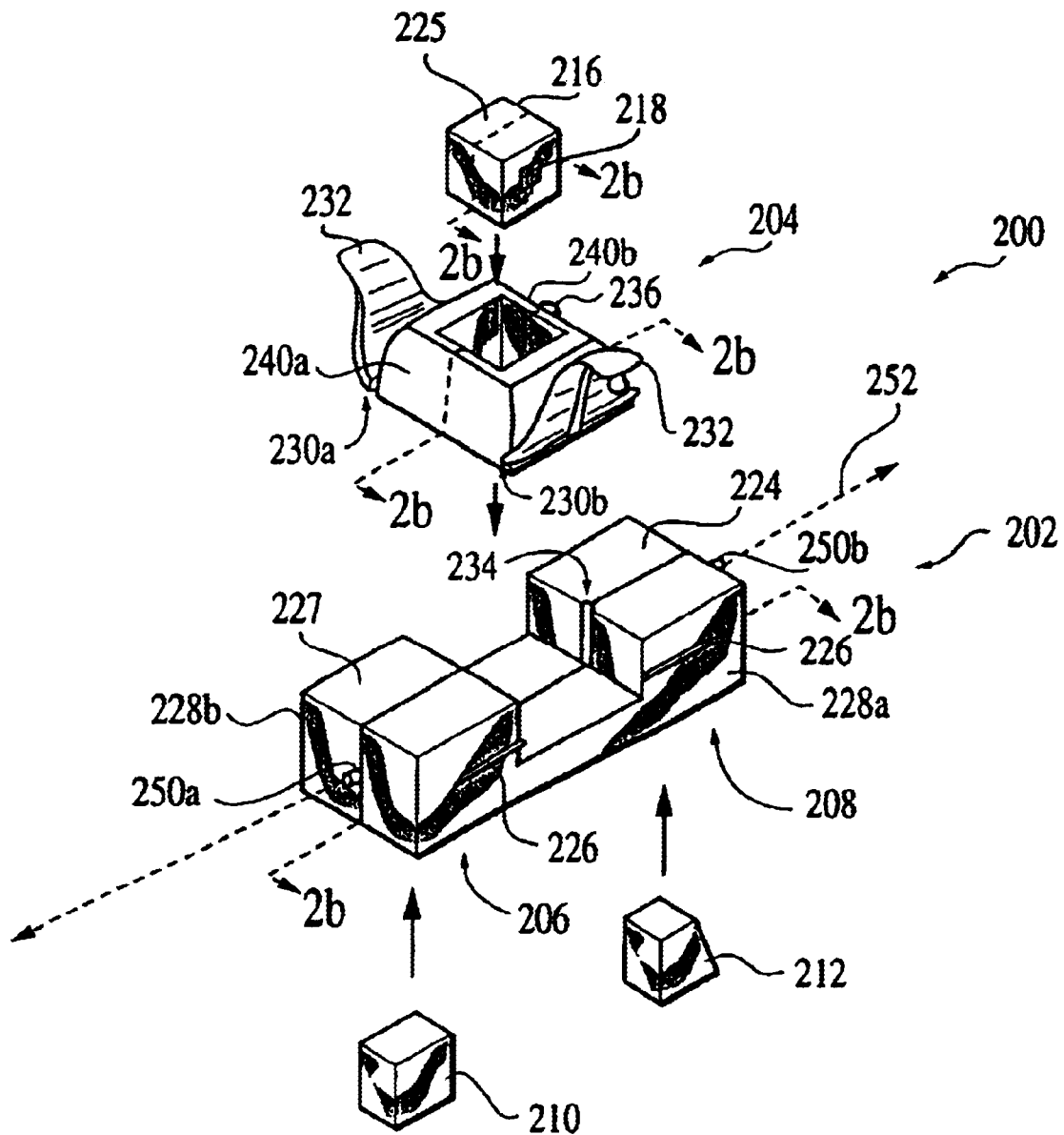
FIG. 2a is a perspective assembly view of a second embodiment of the smart sensor assembly of the invention.
Figure 2B:
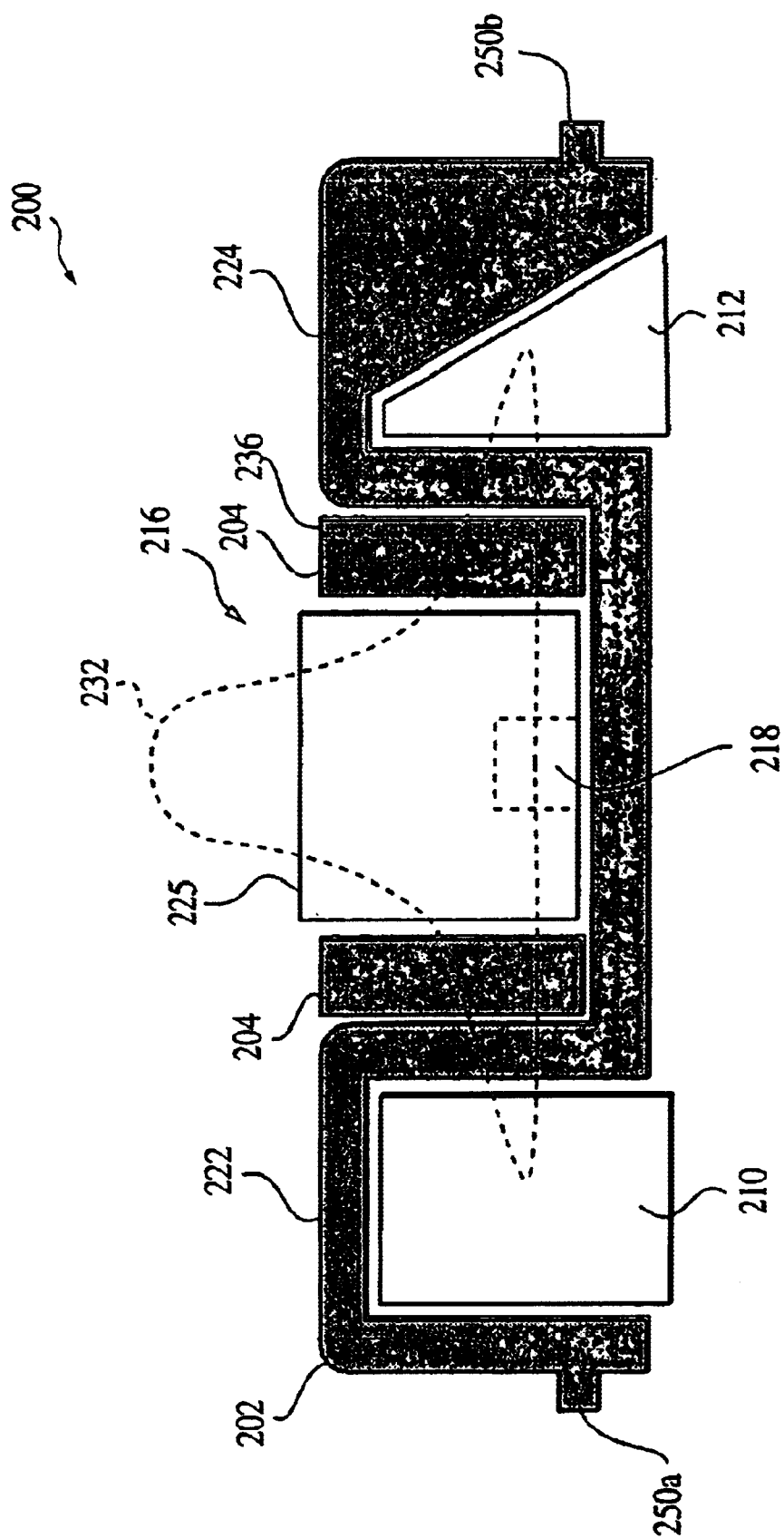
FIG. 2b is a cross-sectional view of the sensor assembly housing of FIG. 2, taken along lines 2—2.
Figure 2C:
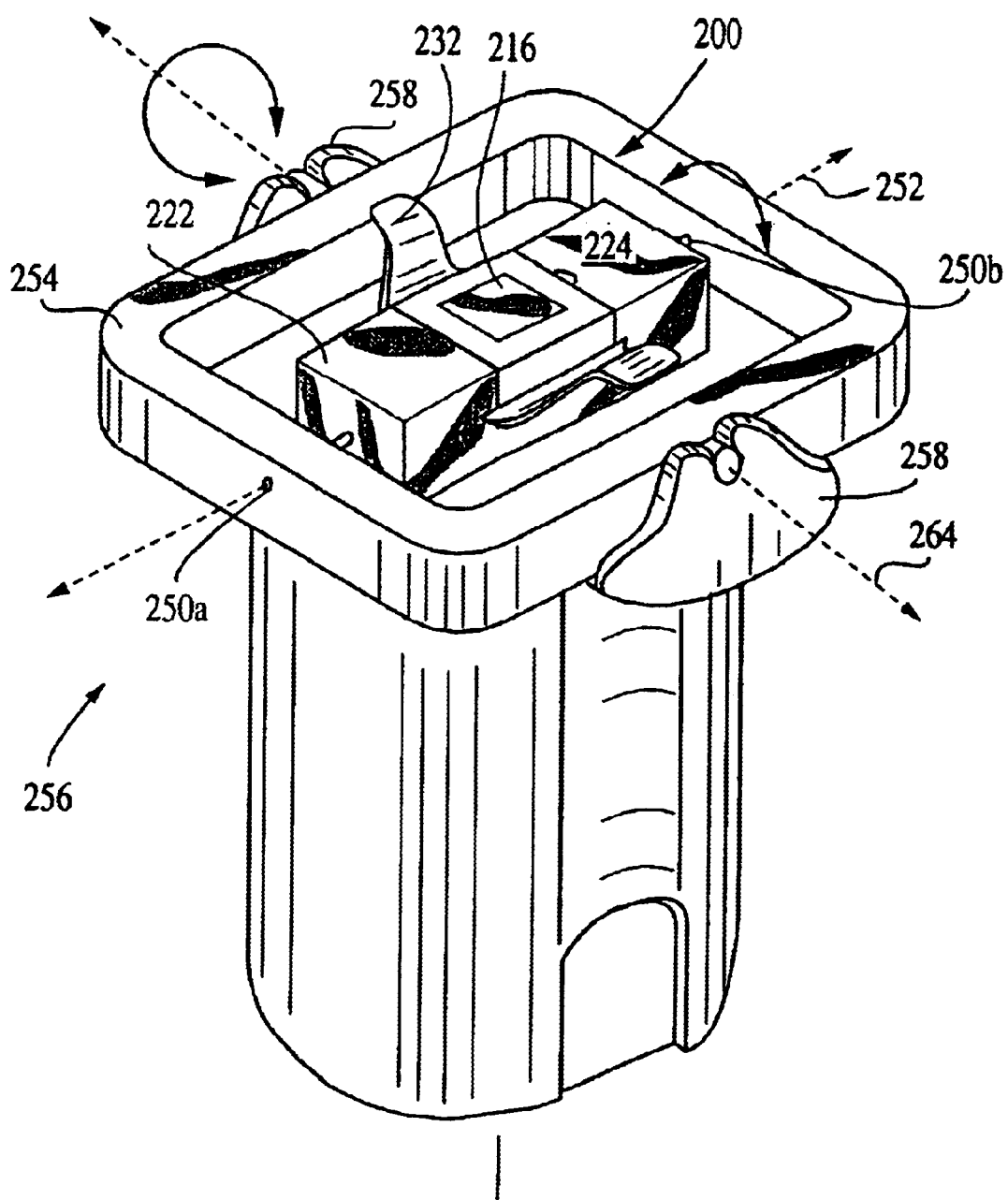
FIG. 2c is perspective view of the sensor assembly of FIG. 2a, shown installed within a gimbal assembly.

Referring now to FIGS. 2a–2c, a second embodiment of the sensor assembly according to the present invention is described. As illustrated in FIG. 2a, the sensor assembly 200 of the second embodiment comprises a two-lobed first housing element 202 and a generally rectangular second housing element 204, the two elements 202, 204 fitting together to form a unitary assembly. The first element 202 includes a pair of adapted recesses 206, 208 in which at least a portion of respective ultrasonic transducer elements 210, 212 are received. The second housing element 204 similarly includes a recess 214 in which the pressure transducer 416 with associated storage device 218 is received. Two ultrasonic transducer elements 210, 212 are used in the illustrated embodiment to measure hemodynamic parameters, and blood velocity. These factors allow correct positioning of the pressure transducer for accurate measurements of blood pressure, as described in Applicant's aforementioned co-pending applications. The pressure transducer 216 comprises a silicon strain beam transducer element which generates an electrical signal in functional relationship (e.g., proportional) to the pressure applied to its sensing surface. Similarly, the ultrasonic transducers 210, 212 comprises piezoelectric (ceramic) devices which are capable of both generating and receiving ultrasonic waves and/or pulses depending on mode. In the illustrated embodiment, the ultrasonic transducers 210, 212 are tuned to generate ultrasonic frequencies centered at 8 MHz and 16 MHz respectively, although other center frequencies, with varying bandwidths, may be used. The transducer elements 210, 212, 216 are frictionally received within the recesses of their respective housing elements 202, 204 via an interference fit of the type well known in the art, although other arrangements (such as adhesives) may be used to retain the transducer elements in the desired position(s).

The housing elements 202, 204 are formed from a low-cost thermoplastic such as polycarbonate although it will be recognized that other materials such as ethylene tetrafluoroethylene (i.e., Tefzel®), Teflon®, PVC, ABS, or even non-polymers may be substituted depending on the desired material and physical properties (such as rigidity, tensile strength, compatibility with certain chemical agents, ultrasonic transmission at certain wavelengths, etc.).

As in the embodiment of FIGS. 1a–1c, the storage device 218 of FIG. 2a comprises an EEPROM, although other types of devices including EPROM, UVEPROM, or even RAM may be substituted. The first and second housing elements 202, 204 are adapted to fit together such that the second element 204 is removable from the first element 202. This aspect of the invention allows for the removal of the pressure transducer element 216 and associated storage device 218 from the first housing element 202, thereby rendering the former disposable if desired. Note however that the first housing element 202 may also be made removable or separable from the local controller 444 (FIG. 4), such that both components are separately disposable (e.g., in the event that it is desired to operate one type of transducer element for a period different than that for the other type of transducer element).

In the illustrated embodiment, the second housing element 204 "snaps" into a channel 220 formed in the first housing element 202 such that the contact surfaces 222, 224 of each the first housing element and that of the pressure transducer 225 are in substantial planar alignment. In this fashion, the contact surfaces 222, 224, 225 each contact the skin (or interposed coupling medium) of the subject concurrently, allowing for ready coupling of each of the transducers to the subject. The snap functionality previously described is accomplished using a series of transverse ridges 226 formed on exterior lateral surfaces 228a, 228b the first housing element coupled with the extending inner edges 230a, 230b of the removal tabs 232 formed on the corresponding sides of the second housing element 204, although it will be appreciated that any other types of arrangements for retaining the second housing element 204 in a given physical relationship with the first housing element 202 may be utilized, such arrangements being well understood by those of ordinary skill in the mechanical arts. For example, other types of snap arrangements (such as one or more raised pins or protrusions, coupled with a complementary detent) may be used. Alternatively, a frangible construction may be employed. As yet another alternative, an adhesive such as a non- permanent silicone-based adhesive, or a frictional interference construction may be used to retain the second housing element 204 within the first 202.

The removal tabs 232 of the second housing element 204 are constructed such that when the tabs are grasped by the user (such as between the thumb and forefinger) and compressed slightly, the extending inner edges 230a, 230b of the tabs 232 disengage slightly from the transverse ridges 226, thereby allowing the second housing element 204 to be removed from the first 202 by pulling it vertically there from. The sidewalls 240a, 240b of the second housing element are designed to allow sufficient flexibility such that when the tabs 232 are compressed, the sidewalls flex and disengage the inner edges 230a, 230b from their respective ridges 226.

The first and second housing elements are also provided with a groove 234 and vertical ridge 236 formed on corresponding mating surfaces of the two components which act to align the second housing element properly, and in one orientation only, within the first housing element. Hence, it will be apparent that the second housing element 204 may only be received within the first element 202 in one orientation, such that the transducer elements 210, 212, 216 are in proper alignment when the assembly 200 is properly assembled.

Figure 4:
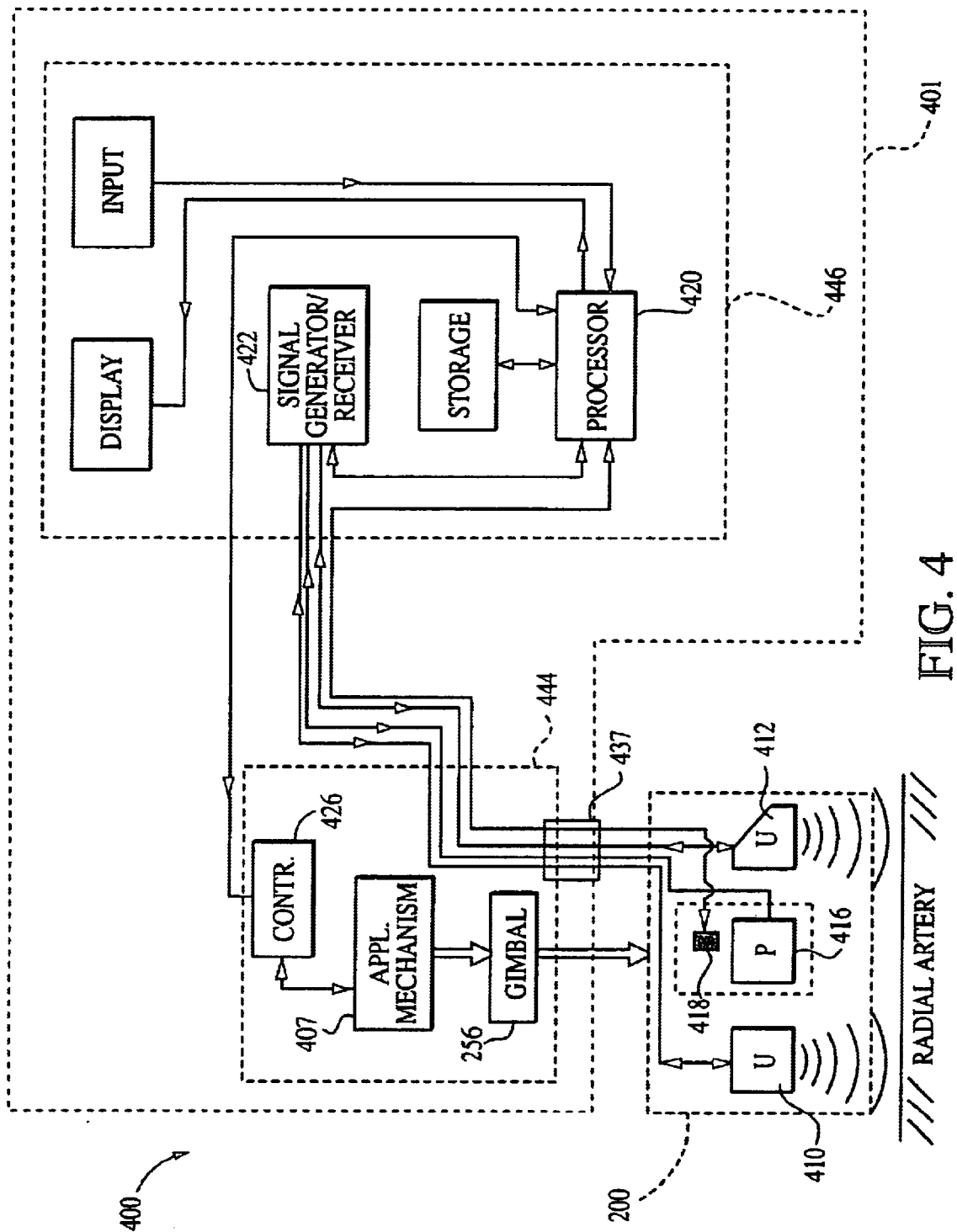
FIG. 4 is a functional block diagram illustrating a first embodiment of a physiologic parameter measurement apparatus incorporating the smart sensor assembly of the invention.

The first housing element 202 is further equipped with a pair of pivot pins 250a, 250b which are disposed linearly and parallel to the longitudinal axis 252 of the first element 202. The pivot pins 250 are received within respective bores (not shown) formed in a first support element 254 of the gimbal assembly 256 as shown in FIG. 2c, the latter being mounted to the local controller device 444 (FIG. 4). This arrangement permits the sensor assembly 200 to rotate around at least the longitudinal axis 252, thereby allowing the active surface of the transducer element 216 (as well as the contact surfaces 222, 224 of the first housing element 202) to orient themselves properly on the surface of the subject's skin. A secondary pivot arrangement 260 transverse to the axis 252 is also provided with respect to a second support element 258 as shown, thereby allowing the sensor assembly 200 to rotate around the transverse axis 264 in the direction 266. Hence, when coupled to the gimbal 256, the sensor assembly 200 is advantageously allowed three distinct degrees of freedom (two rotational, and one in the vertical or normal direction), which permits the ultrasonic transducer elements 210, 212 and the pressure transducer 216 to be correctly oriented with respect to the skin of the subject at all times during the measurement, even when the subject moves during the measurement.

Figure 3:
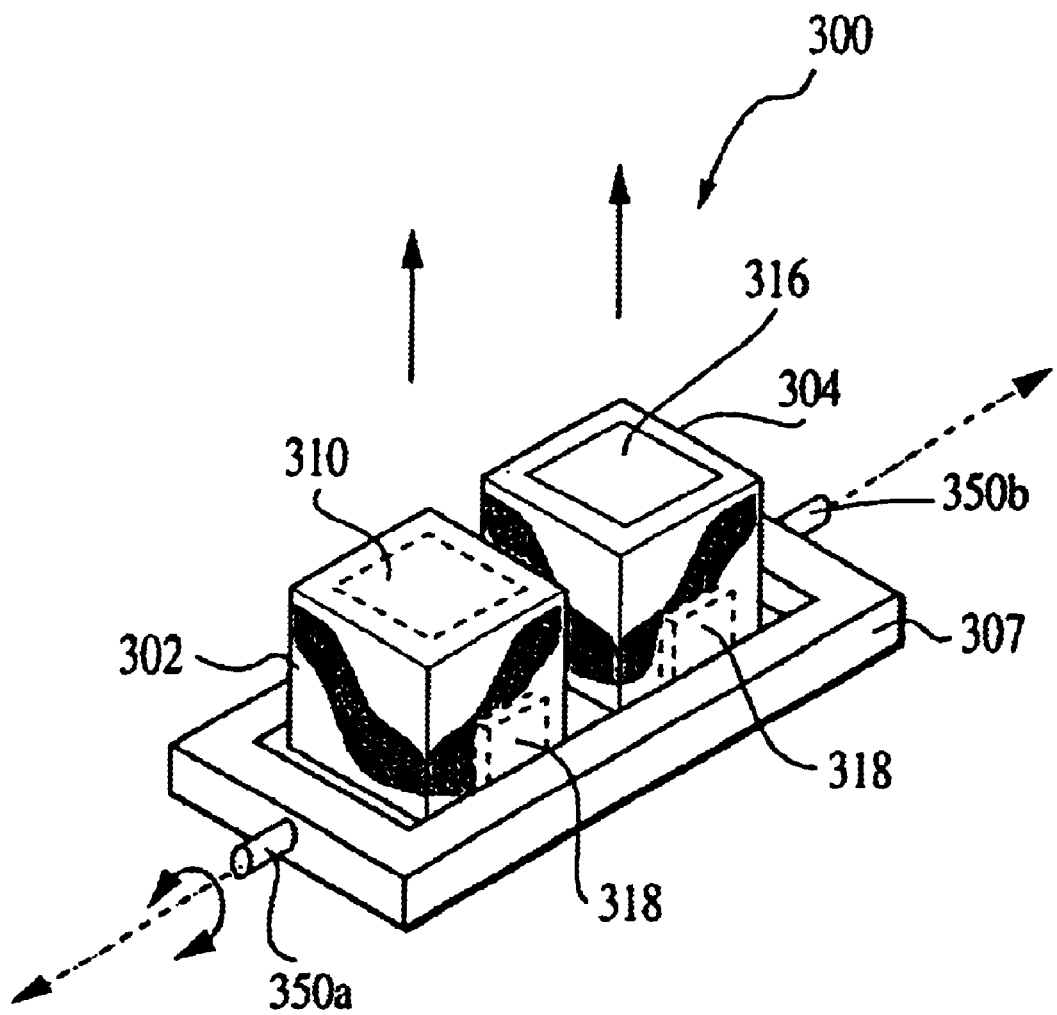
FIG. 3 is a top plan view of a third embodiment of the sensor assembly of the invention, having both removable/disposable pressure and ultrasonic transducers.

Additionally, it will be appreciated that while the embodiment of the sensor assembly 200 of FIGS. 2a–2c includes a generally two-lobed first housing element 202 and second housing element with a single transducer element 216, even other configurations may be used. For example, as illustrated in the embodiment of FIG. 3, a single ultrasonic transducer 310 and single pressure transducer 316 can be used, the two transducers being aligned in a "side-by-side" configuration within the complementary housing elements 302, 304. Hence, the embodiments of FIGS. 1a–3 are merely illustrative of the broader concept of having either or both the pressure transducer and/or ultrasonic transducer element(s) (with any associated storage device) being separable from the local controller and optionally disposable.

Apparatus for Physiologic Assessment

Referring now to FIG. 4, an apparatus for assessing the physiologic parameters of a living subject and incorporating the "smart" sensor assembly of the present invention. In the illustrated embodiment, the apparatus is adapted for the measurement of blood pressure within the radial artery of a human being, although it will be recognized that other physiologic parameters, monitoring sites, and even types of living organism may be utilized in conjunction with the invention in a broader sense.

The apparatus 400 of FIG. 4 fundamentally comprises the sensor assembly previously described used in conjunction with a reusable "host" system 401 which controls and supports the operation of the sensor assembly. Specifically, the sensor assembly is contained within a local controller assembly 444, which is coupled via electrical cable or other communications interface to a remote analysis and display station 446. While the apparatus 400 of FIG. 4 having the sensor assembly 200 of FIGS. 2a–2c is described in detail in the following paragraphs, it will be apparent that the assembly of FIGS. 1a–1c, or alternatively yet another configuration, may be used with equal success.

Further included in the apparatus 400 are a pressure transducer 416 for measuring blood pressure from the radial artery tonometrically; an applanation device 407 coupled to the transducer 416 for varying the degree of applanation (compression) on the artery; two ultrasonic transducers 410, 412 for generating ultrasonic emissions and reflections thereof, these ultrasonic emissions being used to derive blood velocity (and kinetic energy); a signal processor 420 operatively connected to the pressure and ultrasonic transducers 416, 410, 412 for analyzing the signals generated by these transducers and generating a calibration function based thereon; a signal generator/receiver 422 used to generate ultrasonic signals for transmission into the artery, and receive signals from the ultrasonic transducers 410, 412; and a controller 426 operatively coupled to the applanation device 407 and the signal processor 420 for controlling the degree of applanation pressure applied to the artery. The pressure and ultrasonic transducers 416, 410, 412 are arranged within the sensor assembly 200 previously described with respect to FIG. 2 herein. The gimbal 256 is coupled to the sensor assembly 200 and the applanation device 407 as shown in FIG. 2c in order to transfer the applanation force from the device 407 to the sensor assembly 200 and ultimately to the skin of the subject. The applanation mechanism 407 and sensor assembly 200 (along with apparatus necessary to maintain the sensor assembly 200 in position on the subject, such as a wrist brace or band) collectively comprise the local controller assembly 444 which is mounted on the subject's wrist, although it will be appreciated that other configurations may be substituted. Furthermore, the various signal processing and/or electronic components such as the processor 420 and controller 426 may be located within the controller assembly 444 or alternatively located remotely from the subject such as in the monitoring and display station 446 if desired.

The local controller assembly 444 further includes portions of the logic circuit (as described below with respect to FIGS. 7 and 8), which compensates or calibrates the pressure transducer element 416 for offset, temperature effects, and non-linearities characteristic of each individual pressure transducer element. This calibration is advantageously conducted upon the initialization of each new pressure transducer element 416 and associated EEPROM device 418, thereby assuring the adequacy and proper calibration of the apparatus 400 as a whole before use with that new transducer element.

The analysis and display unit 446 comprises display, data analysis, user control, and data storage functions for the apparatus 400 including the display of raw data sensed by the transducer elements, display of parameters calculated based on the raw data by the processor and associated signal processing algorithms, equipment status indications, display of information stored within the storage device 218 of the sensor assembly (such as pressure transducer manufacture date/location, calibration parameters, etc.), name/SSN of the subject being monitored, etc. In one embodiment, the analysis and display station comprises a dedicated device having a CRT, TFT/LCD, LED, or plasma display coupled with a variety of pre-specified control and data storage functions. Alternatively, a laptop or handheld computer having software adapted for performing each of the foregoing functions, or those specifically chosen by the user, may be substituted. It will be recognized that each of the foregoing display, storage, and user control functions are well known to those of ordinary skill in the electronic arts, and accordingly are not described further. Analysis of the signals derived from the sensor assembly 200 is described in the foregoing U.S.pstent spplicstion previously incorporated herein.

The signal generator/reciever 422 generates electrical signals or pulses which are provided to the ultrasonic transducers 410, 412 and converted into ultrasonic energy radiated into the blood vessel. This ultrasonic energy is reflected by various structures within the artery, includeing blood flowing therein, as well as tissue and other bodily components in proximity to the artery. These ultrasonic reflections (echoes) are recieved by the ultrasonic transducers and converted into electrical signals which are then converted by the signal generator/reciever 422 to a digital form (using, e.g., an ADC) and sent to the signal processor 420 for analysis. In the pressent embodiment, the signal processor comprises a microprocessor unit and a digital signal processor (DSP) unit (not shown) in order to facilitate, inter alis, rapid data processing and the control functionality previously described, although it will be recognized that the processor 420 may configured in other ways if desired. Depending on the type of ultrasonic analysis technique and mode employed, the signal processor 420 utilizes its program (either embedded or stored in an external storage device) to anlyze the recieved signals. For example, if the system is used to measure the maximum blood velocity, then the recieved echoes are analyzed for, inter alia, Doppler frequency shift. Alternatively. if the arterial diameter (area) is measured, then an analysis appropriate to the aforementioned A-mode is employed. U.S. patent applications Ser. Nos. 09/342,549 filed Jun. 29, 1999 and 09/534, 900 filed Mar. 23, 2000, previously incorporated by reference herein, describe adaptations of the apparatus 400 for time-frequency and hemodynamic parameter blood pressure measurement, respectively.

Figure 5:
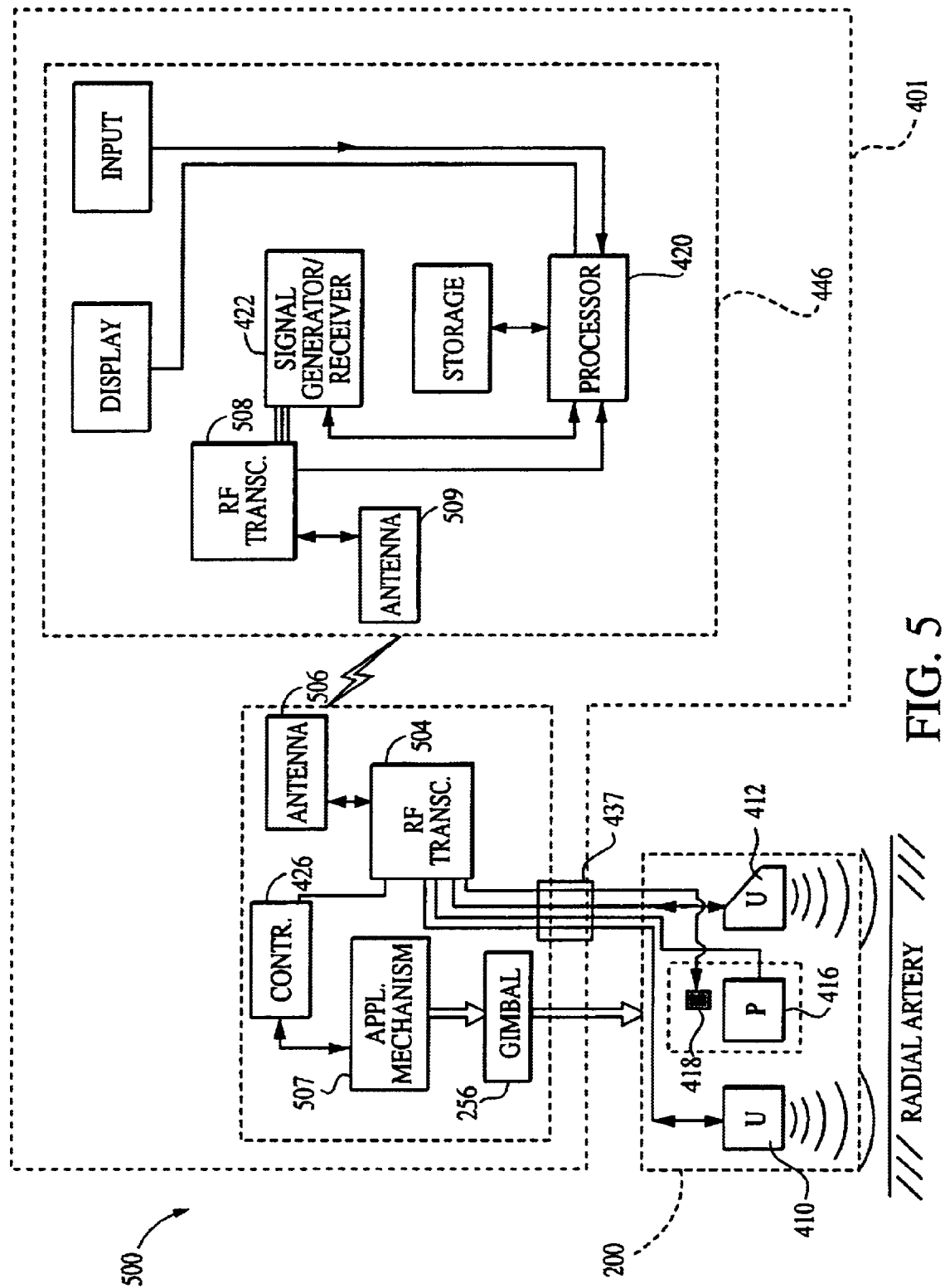
FIG. 5 is a logical block diagram of a second embodiment of the physiologic parameter measurement apparatus of the invention, including a wireless communications link.

FIG. 5 illustrates a second embodiment of the physiologic parameter measurement apparatus of the present invention. In the embodiment of FIG. 5, the system 500 further includes a radio frequency (RF) transceiver chip 504 and associated processing of the type well known in the art for transmitting the information generated by the transducers elements 510, 512 and stored within the storage device 518 to the host device via an associated antenna 506 located on the local control assembly 507 and receiver 508 located on the analysis and display device 523. The antenna 506 and receiver 508 ideally comprise transponders, thereby enabling two-way communication between the local control assembly 507 and the analysis and display unit 523.

In the configuration of FIG. 5, the need for wiring or conductors communicating the electrical signals between the local control assembly 507 and the remote analysis and display unit 523 is advantageously obviated, thereby allowing the patient additional mobility during blood pressure measurement, such as when being transferred from one location in a hospital to another. It will also be recognized that a number of different wireless transmission methodologies (air interfaces) may be employed to transfer data between these entities including, inter alia, point to point transmission via the Infrared Data Association's ("IrDA") infrared based wireless transmission standard; wireless radio frequency ("RF") based local area network ("LAN") connections based on the IEEE 802.11 LAN access standard (including both frequency-hopping and direct sequence spread spectrum variants); the "Bluetooth" 2.45 GHz frequency band based wireless communication specification, and even the Home RF Shared Wireless Access Protocol. The construction and operation of each of these air interfaces is well known in the telecommunications arts, and accordingly is not described further herein.

Figure 6:
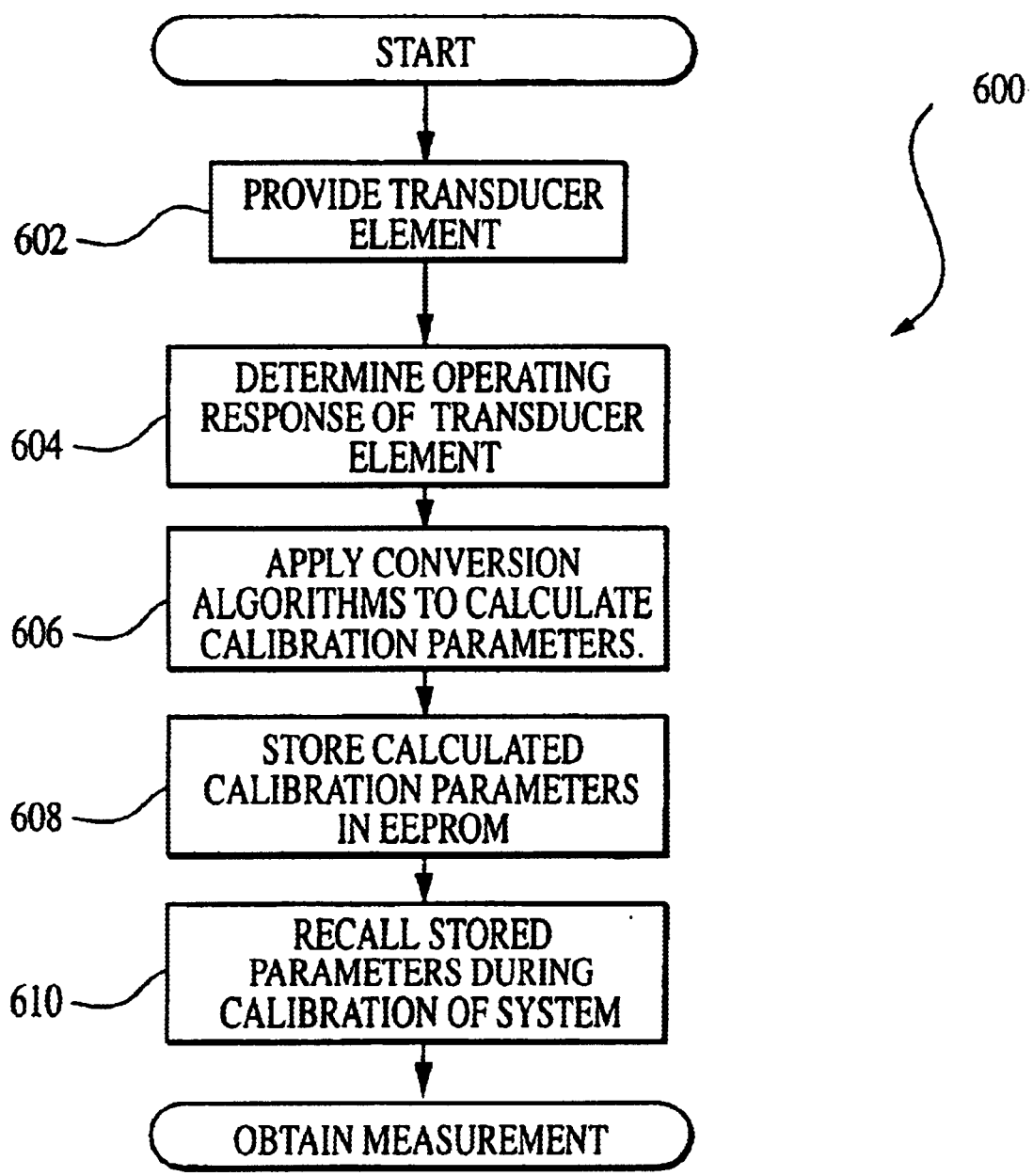
FIG. 6 is a logical flow diagram illustrating one exemplary embodiment of the method of calibrating a disposable sensor element according to the invention.

Referring now to FIG. 6, the method of calibrating a disposable transducer element such as that of FIGS. 2a–2c using its associated storage device is described. It will be recognized that while the following discussion is cast in term of the calibration of a silicon strain beam pressure transducer element, the general principles described herein are equally applicable to wire strain gage transducer elements or yet even other types of sensor elements.

As shown in FIG. 6, the method 600 comprises first providing a transducer element (such as the aforementioned pressure transducer 216 of the embodiment of FIG. 2) having a predetermined operating response per step 602. Next, the operating response of the transducer element is determined in step 604. In the illustrated embodiment of the method, the response of the transducer element is determined by measuring, inter alia, the bridge voltage ($E_b$) and signal output voltage of the transducer element ($E_s$) under varying conditions of temperature and applied pressure. Specifically, $E_b$ and $E_s$ are measured for a series of increasing pressures at a first temperature $T_o$, and then again at a higher or "hot" temperature $T_h$. Table 1 below illustrates this principle graphically. This step 604 is typically but not necessarily performed by the transducer vendor or manufacturer.

exemplary set of calibration parameters, allowable ranges, and conversion algorithms for a typical silicon strain beam pressure transducer element.

TABLE 2

| Calculations for EEPROM | | Range | | Resolution | Units |
|---|---|---|---|---|---|
| Eref = Er | @Po | 4.998 | 5.002 | 0.001 | V |
| Tref = To | @Po | 20.0 | 24.0 | 0.1 | oC |
| Thigh = Th | @Po | 38.0 | 42.0 | 0.1 | oC |
| Vos = Eso | @Po | −5.250 | 5.250 | 0.001 | mV |
| $\text{Vos TC} = \dfrac{Es4 - Eso}{Th - To}$ | @Po | −30.0 | 30.0 | 0.1 | uV/oC |
| Ebo = Ebo | @Po | 1.0000 | 1.5000 | 0.0001 | Volts |
| $\text{Ebo TC} = \dfrac{Eb4 - Ebo}{Th - To}$ | @Po | 1.000 | 2.000 | 0.001 | mV/oC |
| $\text{Sens} = \dfrac{Es2 - Eso}{P2 - Po}$ | Rel to P2 | 35.0 | 80.0 | 0.1 | uV/mmHg |
| $\text{Lin Error} = \dfrac{100[(Es3 - Eso) - 3(Es2 - Eso)]}{3(Es2 - Eso)}$ | @To | −1.50 | 1.50 | 0.01 | % |
| Ecal = Ecal | @Po | 5.50 | 10.60 | 0.01 | mV |

Assumptions:
Vos TC and Ebo TC are independent of pressure.
Sensitivity is independent of temperature.
where:
$E_{ref}$ = Reference voltage used by vendor at measurement (V)
$T_{ref}$ = Reference temperature used by vendor (degrees C.)
$T_h$ = "High" temperature used by vendor during raw data measurement (degrees C.)
$V_{os}$ = Offset voltage of transducer (bridge) at zero applied pressure and Tref (mV)
$V_{osTC}$ = Temperature correction factor for offset voltage of bridge (mV/degree C.)
$E_{b0}$ = Bridge voltage at $T_{ref}$ (V)
$E_{b0TC}$ = Temperature correction factor for bridge voltage (mV/degree C.)
Sens = Sensitivity of bridge to pressure change (uV/mmHg)
Lin Error = Linearity error or non-linearity (%)
$E_{cal}$ = Shunted output voltage of bridge (mV)

TABLE 1

| Temp. | Press | Eb | Es | Er | Es-15K |
|---|---|---|---|---|---|
| oC. | mmHg | V | mV | V | mV |
| To | Po | 0 | Ebo | Eso | Eref | Ecal |
| To | P1 | 50 | Eb1 | Es1 | Eref | |
| To | P2 | 100 | Eb2 | Es2 | Eref | |
| To | P3 | 300 | Eb3 | Es3 | Eref | |
| Th | P4 | 0 | Eb4 | Es4 | Eref | |
| Th | P5 | 50 | Eb5 | Es5 | Eref | |
| Th | P6 | 100 | Eb6 | Es6 | Eref | |
| Th | P7 | 300 | Eb7 | Es7 | Eref | |

Next, in step 606, a series of conversion algorithms are applied to the "raw" transducer response data obtained in step 604 to convert the response data to calibration parameters useful for calibrating the pressure transducer in-situ during operation. Allowable ranges for the resulting calibration parameters are also specified. Table 2 illustrates an where:

$E_{ref}$=Reference voltage used by vendor at measurement (V)

$T_{ref}$=Reference temperature used by vendor (degrees C)

$T_h$="High" temperature used by vendor during raw data measurement (degrees C)

$V_{os}$=Offset voltage of transducer (bridge) at zero applied pressure and Tref (mV)

$V_{osTC}$=Temperature correction factor for offset voltage of bridge (mV/degree C)

$E_{b0}$=Bridge voltage at Tref (V)

$E_{b0TC}$=Temperature correction factor for bridge voltage (mV/degree C)

Sens=Sensitivity of bridge to pressure change (uV/mmHg)

Lin Error=Linearity error or non-linearity (%)

$E_{cal}$=Shunted output voltage of bridge (mV)

The conversion algorithms of Table 2 are derived based on the definition of the various calibration parameters (Table 3. below), and the raw transducer response data. For example, in the case of the temperature correction factor for the bridge voltage ($E_{b0TC}$), the bridge voltage taken at the reference temperature $T_0$ and zero pressure, or $Eb_0$, is subtracted from the bridge voltage taken at the "hot" temperature "$T_h$" and zero pressure ($E_{b4}$), the resultant of which is divided by the difference between the hot temperature and the reference temperature (i.e., $T_h$ minus $T_0$) to produce $E_{b0TC}$. The derivation of the other conversion algorithms is generally analogous, and easily determined by those of ordinary skill in the electronic arts.

Next, in step 608, the calculated calibrations parameters (Table 3 below) are stored within the storage device (e.g., EEPROM) of the transducer element for later recall during calibration/operation (step 610). Appendix I illustrates exemplary code useful for extracting the calibration parameters of Table 3 for a pressure transducer element from the EEPROM associated therewith.

TABLE 3

EEPROM DATA

| | | |
|---|---|---|
| Er | 5.002 | V |
| To | 24.9 | oC |
| Th | 40.0 | oC |
| Vos | 3.4999 | mV |
| Vos TC | 29.9 | uV/oC |
| Ebo | 1.4999 | V |
| Ebo TC | 1.960 | mV/oC |
| Sens | 80.0 | uV/mmHg |
| Lin Error | −1.99 | Percent |
| Ecal | 10.60 | mV |

Figure 7:
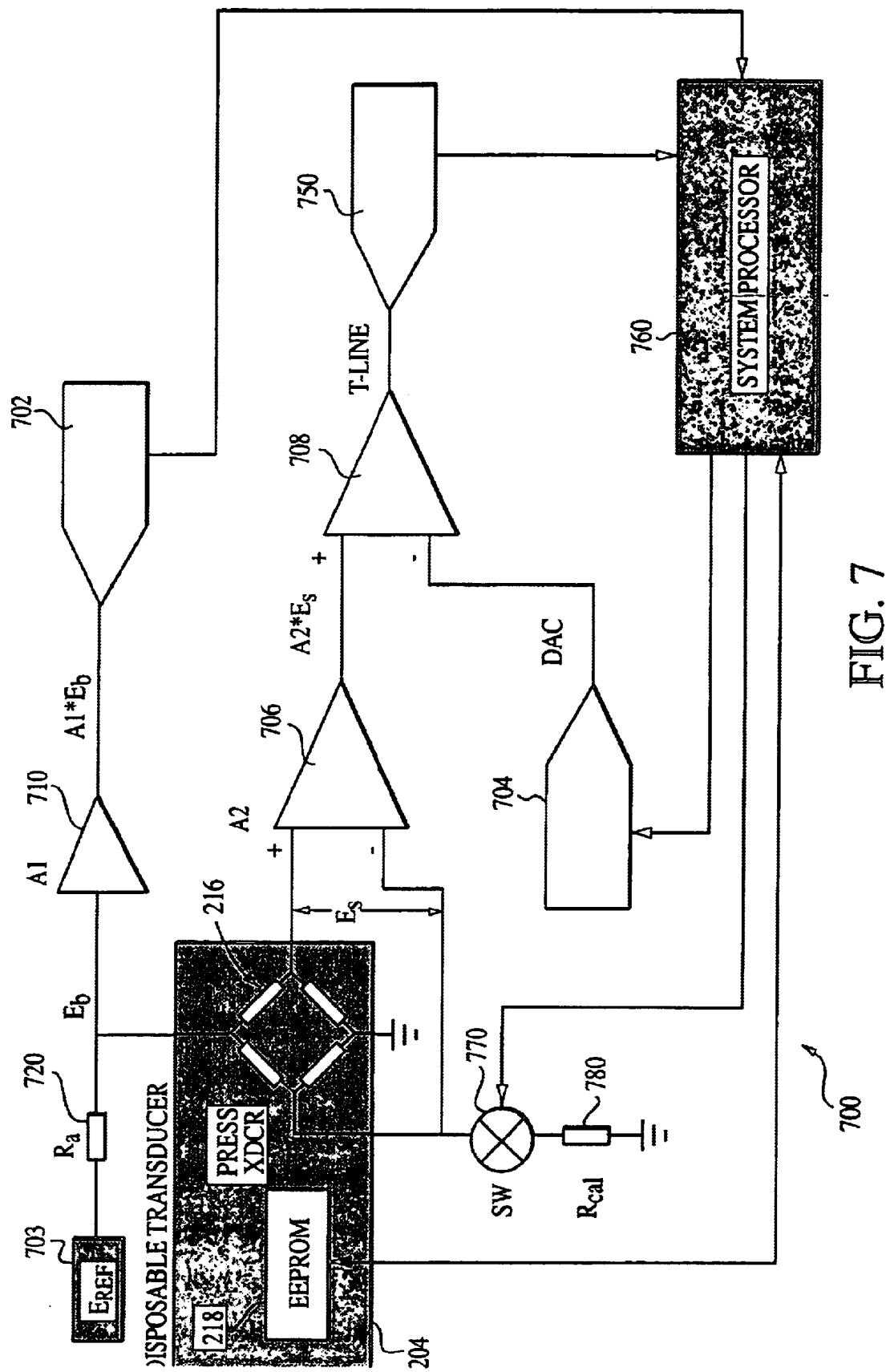
FIG. 7 is a schematic diagram of a first embodiment of the logic circuit of the invention.

Referring now to FIG. 7, a first embodiment of the logic circuit used for effectuating the calibration of the pressure transducer element(s) as described with respect to FIG. 6 above is disclosed.

In the embodiment of FIG. 7, the circuit 700 comprises an analog circuit having a pressure transducer element 216 represented in the form of an electrical bridge, an EEPROM 218, a span compensation resistor $R_a$, 720, reference voltage $E_{ref}$ 703, first and second analog-to-digital converters (ADC's) 702, 750, digital-to-analog converter (DAC) 704, three operational amplifiers 706, 708, 710 of the type well known in the electronic arts, a system processor 760, which can be any microprocessor, microcontroller, or even a DSP device, electronic analog switch 770, and a precision shunt resistor $R_{cal}$ 780. The voltage output of the pressure transducer (bridge) 716 is input to a first stage operational amplifier 706 which amplifies the output of the pressure transducer. The amplified output is input to a second stage amplifier 708, along with the output of the DAC 704, which is subtracted from the transducer signal. The output of the second stage amplifier 708 represents the temperature compensated, zero offset output signal of the circuit 700. In operation the system processor 760 reads the data stored in the EEPROM 218, and sets the DAC 704 to eliminate the offset. Since the offset is a function of temperature, the system processor 760 also reads the output of the first ADC 702, which is sensing the bridge voltage $E_b$ of the pressure transducer 716. The bridge voltage varies with temperature, and the correlation between its variation wand the offset variation with temperature is stored in the EEPROM. Since this variation is small, it is amplified by the third stage amplifier 710, before being read by the first ADC 702. As used herein, term "offset" refers to the output voltage of the bridge 216 at zero applied pressure under specified conditions of temperature. The second ADC 750 is used to convert the final analog output of the second stage amplifier 708 to a digital representation of the blood pressure. In this embodiment, the system processor reads the EEPROM in the disposable transducer 216, to obtain the transducer sensitivity (Sens). This factor is used to scale the output of second stage amplifier 708 in the digital domain so that a known relationship of the output of the amplifier 708 exists in mV per mmHg.

In the illustrated embodiment, the span compensating resistor $R_a$ 720, value is chosen to be 1000 ohms based on the bridge impedance, span TC, and reference voltage $E_{ref}$ 703, which is chosen to be 5 V. It will be recognized, however, that a range of values for $R_a$ are possible from a few hundred ohms to several thousand ohms. Reference voltages other than 5 V may also be used. The main functions of resistor $R_a$ 720, are to temperature compensate the span sensitivity of the transducer to temperature, and to provide signal $E_b$, which provides an output which is a function of the temperature of the bridge. The calibration and functionality of the transducer and the system can be checked by periodically turning on the analog switch 770, which shunts one side of the bridge with precision resistor $R_{cal}$ 780. In one embodiment, this operation is initially performed at the time of manufacture, and the result is stored in the EEPROM as $E_{cal}$. The resistor 780 is selected to have a near zero TC, and a precise value that gives a response approximately equal to the equivalent of 100 mmHg. When the disposable transducer element is first connected, the system processor turns on the switch 770 and reads the output of the circuit 700. It then compares the value obtained with $E_{cal}$ which is stored in the EEPROM. If the results match within specified limits, then system accuracy is ensured. Note that this calibration verification generally is performed when the sensor is off the wrist of the subject. Since the system can control and sense the applanation of the sensor, this condition is ensured, and calibration will typically be checked prior to a blood pressure measurement interval.

During operation, the bridge voltage $E_b$ of the circuit 700 is sampled at an interval of once per second, and the input value to the DAC recalculated in order to continually update the DAC output provided to the second stage amplifier 708. In this fashion, the output of the bridge (transducer element) is continually compensated for temperature.

Figure 8:
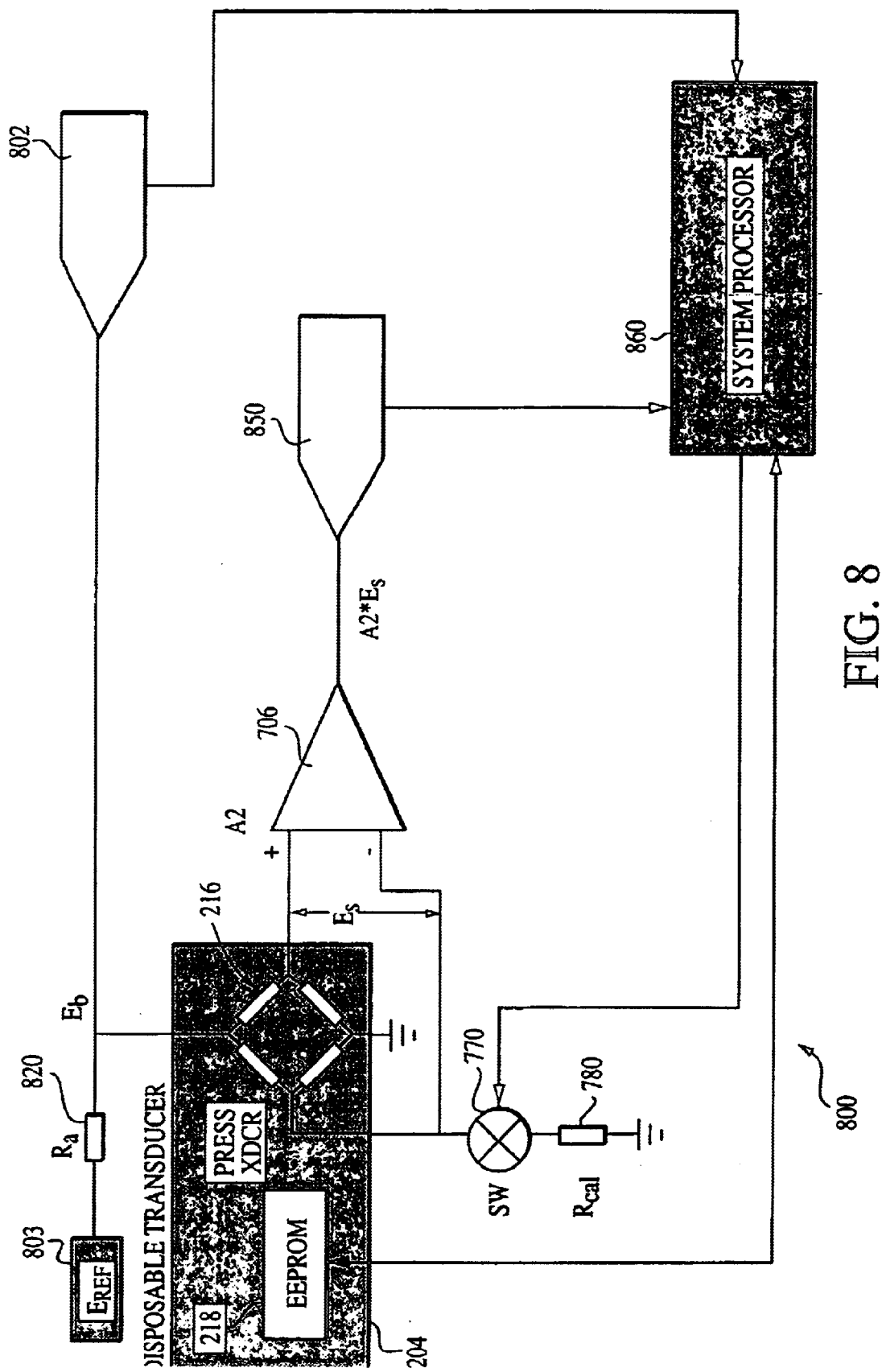
FIG. 8 is a schematic diagram of a second embodiment of the logic circuit of the invention.

In a second embodiment of the logic circuit 800 shown in FIG. 8, portions of the functionality of the circuit of FIG. 7 are alternatively accomplished using higher resolution first and second A/D converters 802, 850 to read the output of the bridge amplifier 806, and the bridge voltage $E_b$. Rather than subtracting out the offset voltage, and the offset variation with temperature in analog circuitry, the embodiment of FIG. 8 digitizes both the signal and the error terms, and does the subtraction in software running on the system processor 860, as is well known in the art. Temperature variations of the bridge 216 are sensed by reading $E_b$ with the first ADC 802. Corrections to the output signal are accomplished in the digital domain by the system processor 860. Note that in yet another alternate embodiment (not shown), one A/D converter and an analog multiplexer are used in place of the first A/D converters 802, 850 of the embodiment of FIG. 8.

Appendix II hereto illustrates various exemplary applications of the smart sensor assembly of the invention, including storing data that enhances sensor and system performance and reliability. It is noted that the applications described in Appendix II are not exhaustive, but rather merely illustrative of the broader concept of the invention disclosed herein.

Referring to Appendix II, Items 1 through 17 therein represent exemplary data that is encoded on the EEPROM during sensor manufacturing according to the present embodiment. Each of these items is described in greater detail below with reference to Appendix I. Note that each of these Items can be considered optional, and furthermore that other configurations (such as different coding schemes, ranges/bits assigned to each parameter, etc.) may be used consistent with the invention.

Item Description
1. Data is encrypted on the EEPROM 116 using a 32-bit encryption key of the type well known in the cryptographic arts. This encryption frustrates unauthorized access to the data present on the EEPROM after encoding. In one embodiment, data is encrypted on the EEPROM using a 32-bit key, and a 32-bit vendor verification code (Appendix II, Item 2). Unless the verification code matches, the system will reject the sensor as a non-matching or non-acceptable sensor. The encryption key is the public part of the key. It is combined with the private part known only to the sensor vendor and customer, and is used to encrypt the data stored on the EEPROM. Sensors which have data which is not encrypted or encrypted incorrectly are rejected by the system upon startup.
2. A 32-bit hexadecimal vendor verification code is provided within the EEPROM 116. Unless the verification code of the sensor assembly matches that stored in the host system 401 (FIG. 4), the host system will reject the sensor as being non-compatible. In this fashion, use of the sensor assembly with a non-compatible host, or vice versa, is prevented, thereby removing a potential source of error in the blood pressure readings obtained from a subject.
3. The manufacturing location is encoded on the sensor. Up to 255 different locations may be coded in the illustrated embodiment. This information may be used for inventory purposes, to track defective lots of items, etc.
4. The date of manufacture is encoded. This date along with the real date derived from a real time clock chip (not shown) in the sensor/blood pressure measuring instrument allows rejection of any sensor assembly that is beyond its shelf life specification (for example, 2 years) when the sensor is connected to instrument. Hence, an "out of date" sensor assembly cannot be used with any host device, even if compatible.
5. The vendor lot code is encoded in the sensor. Since the manufacturing date and location is also encoded, multiple lots per day can be tracked using the present invention.
6. A unique serial number for each senor assembly (and/or each specified transducer element) may also be encoded. The 32-bit field of the illustrated embodiment allows up to 4.295 billion combinations.
7.–15. Items 7–15 characterize the performance of the transducer and allow calibration, linearization, and temperature compensation of the transducer when it is connected to the system. As illustrated in Appendix II, Items 7–15 represent the values of $V_{ref}$, $T_o$, $T_h$, and $V_{os}$, $V_{os\ TC}$, $E_{b0}$, $E_{b0TC}$, Sens, $E_{cal}$, and Lin Error, respectively, as previously described with respect to FIG. 6. Each sensor will have unique values for these items due to manufacturing tolerances. Note that $E_{b0}$ and $E_{b0TC}$ advantageously allow the system the ability to measure the temperature of the sensor directly, and perform calibration of the system based thereon. When used on the radial artery, this temperature will be approximately equal to the patient skin temperature at the wrist when the sensor is in contact with the wrist.
16. A common validation test for pressure transducers is to shunt one side of the bridge with a precision resistor, which causes the bridge to output a full-scale reading. In the present embodiment, this procedure is performed at the time of manufacture, and the actual resulting bridge output for each sensor assembly (as well as any critical test parameters, if desired) encoded into its corresponding EEPROM 116. This same test is then performed in the blood pressure measuring system when the sensor is connected thereto, which validates the accuracy of the sensor electronically. The result of this validation is also optionally stored in the sensor storage device.
17. The ultrasound signals generated by the ultrasonic transducer elements are processed by the system and play a fundamental role in both the placement and positioning of the transducer element(s) and the accuracy of the pressure signal derived from the pressure transducer. A "quality" factor for these processed signals is stored in the EEPROM. This quality factor is derived by the signal processing algorithms and represents the S/N (signal to noise ratio) of the ultrasound signals, as is well known. The higher the S/N, the better accuracy the overall system can achieve.

Referring again to Appendix II, Items 18 through 35 therein represent exemplary data that the exemplary ultrasonic blood pressure measuring system used in conjunction with the sensor of the present invention writes to the EEPROM 116 during the time that the sensor assembly is connected to the host system. These items are described in greater detail below.

Item Description
18. (including Items 19–22) When a sensor is first connected to the blood pressure measuring system, the host system reads the first "n" (e.g., 10) items from the sensor's storage device 116, and first validates that the transducer is a compatible sensor as previously described. The host system then utilizes the sensor calibration information to adjust the system electronics accordingly to optimize the performance of the system for that sensor. The date and time of first connection is also written to the sensor. Once this occurs, the pressure calibration validation test of the present embodiment is performed which mimics the test performed at the time of manufacturing by shunting the bridge with the same value used on the sensor manufacturing line. The result is stored in the sensor. Additionally, the measuring system also optionally includes separate EEPROMs or other storage devices in, inter alia, the sensor positioning head and the system enclosure, which allows these devices to retain unique information such as their own serial numbers or calibration parameters. Such serial numbers may also be stored in the sensor, thereby allowing for tracing the specific measuring system/ positioning head the sensor was being used with at a given time.
23. If any one or more of the tests previously described fail, a code is written back to the sensor indicating what the error(s) were. Table 4 illustrates exemplary error codes, although other codes and arrangements may be used.

TABLE 4

| Code | Error |
| --- | --- |
| 0 | Sensor OK |
| 1 | Non VW Sensor |
| 2 | EEPROM read/write failure |
| 3 | US sensor failure |
| 4 | Cal Test Failure |
| 5 | Railed High |
| 6 | Railed Low |
| 7 | (Reserved) |
| 8 | (Reserved) |
| 9 | (Reserved) |

24. The total time that the sensor is in an electrically powered state is also stored in the sensor. In the present embodiment, this data field is updated within the storage device at periodic intervals (such as every minute), although other schemes for triggering updates, and update frequencies, may be used if desired.

25. The total time that the sensor is performing measurements while powered (as opposed to merely being in an electrically powered state), may also be stored in the sensor storage device. As above, this field is updated on at a periodic interval.
26. The remaining allocated power on time may also be written to the sensor storage device. In an exemplary embodiment, this time is the measurement time (such as 24 hours) plus an additional time (3 hours, for example) to support device setup, although other arrangements may be used.
27. The remaining run time may also be stored in the sensor storage device. In one embodiment, this field is the difference between 24 hours and the actual run time. The field is optionally updated on a periodic basis as previously described.
28. The total number of measurement events is also stored in the sensor storage device. One measurement event is defined in the present embodiment as the start of a measurement cycle to the end of a measurement cycle. The cycle can be any length of time.
29. The total number of "power on" cycles that a sensor sees is stored in the sensor storage device. In one embodiment, the power on/off switch on the instrument is electronic in nature, thereby facilitating counting the number of such events and storing them within the EEPROM. In another embodiment, the voltage at a certain node within the circuitry is sensed; when the voltage level exceeds a predetermined value (corresponding to the fully powered-up state of the sensor), another event is recorded. Many other arrangements are possible, all being well understood by those of ordinary skill in the electronic arts.
30. The sensor replacement code is also stored in the sensor. Examples of sensor replacement codes are shown in the Table 5 herein. By utilizing the run time and power on time data as well as the initial power on date and time, the duration of sensor use may be accurately monitored and controlled In one exemplary embodiment, a utilization window of a predetermined interval (e.g., 30 hours) from initial power up time) may be defined. Even if the sensor were not used during the interval, it would expire concurrent with the expiration of the interval. Within the interval, shorter periods corresponding to power-on time and measurement time may be defined. For example, up to 24 hours of actual measurement time, and 27 hours of actual power up time, would be allowed during the aforementioned 30 hour interval.

TABLE 5

| Code | Error |
|---|---|
| 0 | Sensor OK |
| 1 | Non VW Sensor |
| 2 | 24 Hr measurement time expired |
| 3 | 27 Hr power on time expired |
| 4 | 30 Hr utilization time expired |
| 5 | Shelf life expired |
| 6 | Wrong mechanism |
| 7 | Wrong instrument |
| 8 | Wrong Patient |
| 9 | Wrong Unit |
| 10 | Wrong Hospital |
| 11 | (Reserved) |

It is noted that the sensor replacement and error codes previously described (Items 23 and 30) are useful for service issues. In one possible scenario, failure analysis may be performed on one or more subsets of a given sensor population (such as those sensors which failed during use over a given period of time at a given health care facility). The contents of the sensor's EEPROM may be downloaded to allow analysis of the individual failures. For example, if a large percentage of the aforementioned sensor failures occurred when the sensors were connected to a particular mechanism, the likely source of the failures, i.e., the common mechanism, could be divined as uniquely identified by its EEPROM serial number. Other scenarios are possible, all considered to be within the scope of the present invention.

31.–35. During use, the blood pressure measurement system periodically checks the pressure sensor calibration (ideally, not during measurements) and write the result of one or more such tests to the sensor storage device. Also, during measurements, the system periodically writes the blood pressure, applanation value, and time and date to the sensor storage device. This data is subsequently retrievable and useful in evaluating the actual performance of the sensor and the measurement system, which might prove useful in a variety of circumstances (such as, inter alia, medical malpractice or products liability litigation).

Items 36 through 39 of Appendix II illustrate additional data which may optionally be recorded within the storage device according to the present invention. These items can be configured by the health care provider/physician if desired. For example, the hospital name and care unit as well as the patient name and attending may be entered into the storage device(s) of the sensor and/or measurement system. If the hospital staff wanted to be sure that a sensor was only used on one patient, or only on a particular individual, or only within a specific ward or department (such as the Operating Room or Intensive Care Unit), the system may be configured to facilitate this. If use outside of the allowed parameters was detected, the sensor would be rejected, and the appropriate replacement code stored in the sensor's EEPROM.

It is also noted that since the present embodiment stores data in the sensor itself, the utilization of the sensor can be controlled across multiple mechanisms, systems, and power down events. Additional protection may also be gained by downloading a write authorization code to the sensor. For example, if attempts were made to write to the sensor to reset its run time, and the correct write authorization code was not utilized, the system would reject the sensor. The 32-bit encryption algorithm previously described further thwarts such attempts. Other security or cryptographic techniques well known in the art may be used to implement this protective functionality as well.

Method of Operation

Figure 9:
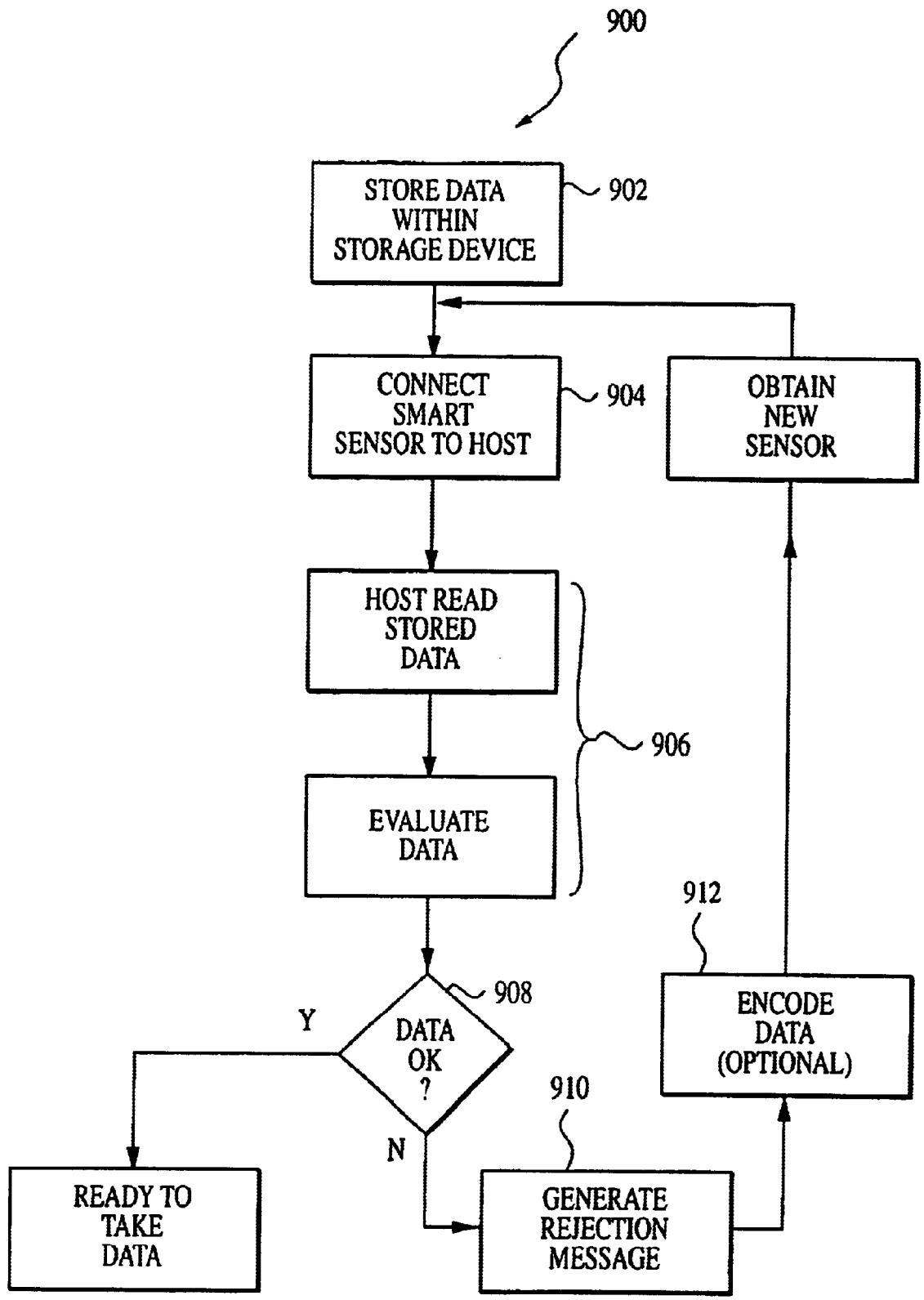
FIG. 9 is a flow diagram illustrating one embodiment of the method of evaluating the acceptability of the smart sensor assembly of the invention in conjunction with the physiologic parameter measurement apparatus of FIG. 4.

Referring now to FIG. 9, a first embodiment of the general method of evaluating the acceptability of a disposable sensor assembly according to the present invention is described. It is noted that the embodiment of FIG. 9 is merely illustrative of the broader concept of the invention, and is not meant to be restrictive in any way. As shown in FIG. 9, the method 900 comprises a first step 902 of storing data within the storage device (e.g., EEPROM) of the sensor assembly. As discussed with reference to Appendix II above, the data may take on any number of forms including the serial number or other identifying data of the probe, its date of manufacture, powered-on time to date, etc. Such data may be loaded upon manufacture, during operation/testing, or both. In step 904, the smart sensor assembly is connected to the "host" ultrasonic measurement system 401 (FIG. 4) previously described. Next, in step 906, the data stored within the sensor storage device is read by the host and evaluated for compatibility between sensor and host (e.g., is the sensor of the type designated for use with a particular host), remaining lifetime, suitability of application (e.g., is the sensor suitable for use with the given patient or at the location indicated by the host), etc. If the sensor assembly (or component thereof) is somehow incompatible or otherwise restricted from use with the host in step 908, the host generates an indication of rejection (step 910) and optionally encodes data within the host and/or sensor assembly storage device to this effect per step 912. The user is then prompted to change the sensor assembly or incompatible component in steps 914 and 916.

Figure 10:
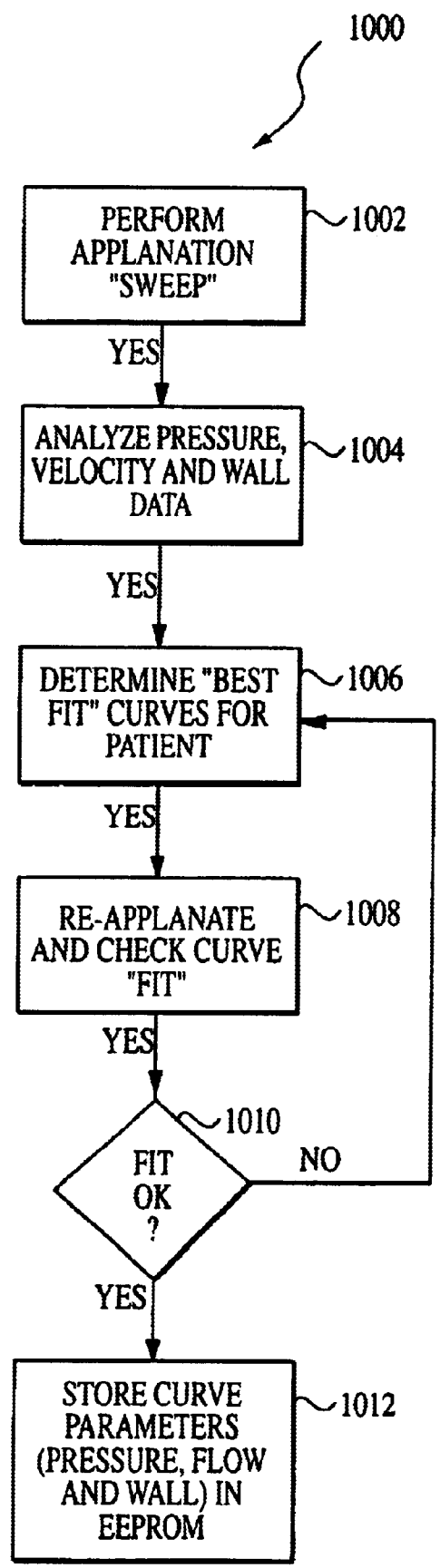
FIG. 10 is a flow diagram illustrating one embodiment of the generalized method of encoding and storing data related to an applanation measurement performed on a patient within the sensor assembly of the invention.

Referring now to FIG. 10, one embodiment of the data encoding and storage method of the present invention is described. While the following description is cast in terms of a tonometric non-invasive blood pressure measurement, it will be apparent to those of ordinary skill that the methodology of FIG. 10 may be adapted to other types of parametric measurements and devices.

As shown in FIG. 10, the method 1000 comprises a first step 1002 of performing an applanation "sweep" using the ultrasonic blood pressure measurement system previously described. When data from the sweep is obtained, the pressure, velocity, and wall (diameter) data is analyzed per step 1004. Based on this analysis, the "best fit" curves for the patient are determined per step 1006. These best fit curves are determined using any one of a number of different methods, one exemplary method being described herein with reference to FIG. 11. Next, in step 1008, the patient is again applanated using the measurement system to determine the adequacy of the curves generated in step 1006. If the curves are adequate (as based on predetermined criteria such as those described below with reference to FIG. 11, or other selected criteria) in step 1010, the curves are then stored per step 1012 in the storage device of the sensor assembly. Stored data may include the measured pressure, blood velocity, and arterial diameter, or any other parameters related to the applanation as desired.

Figure 11:
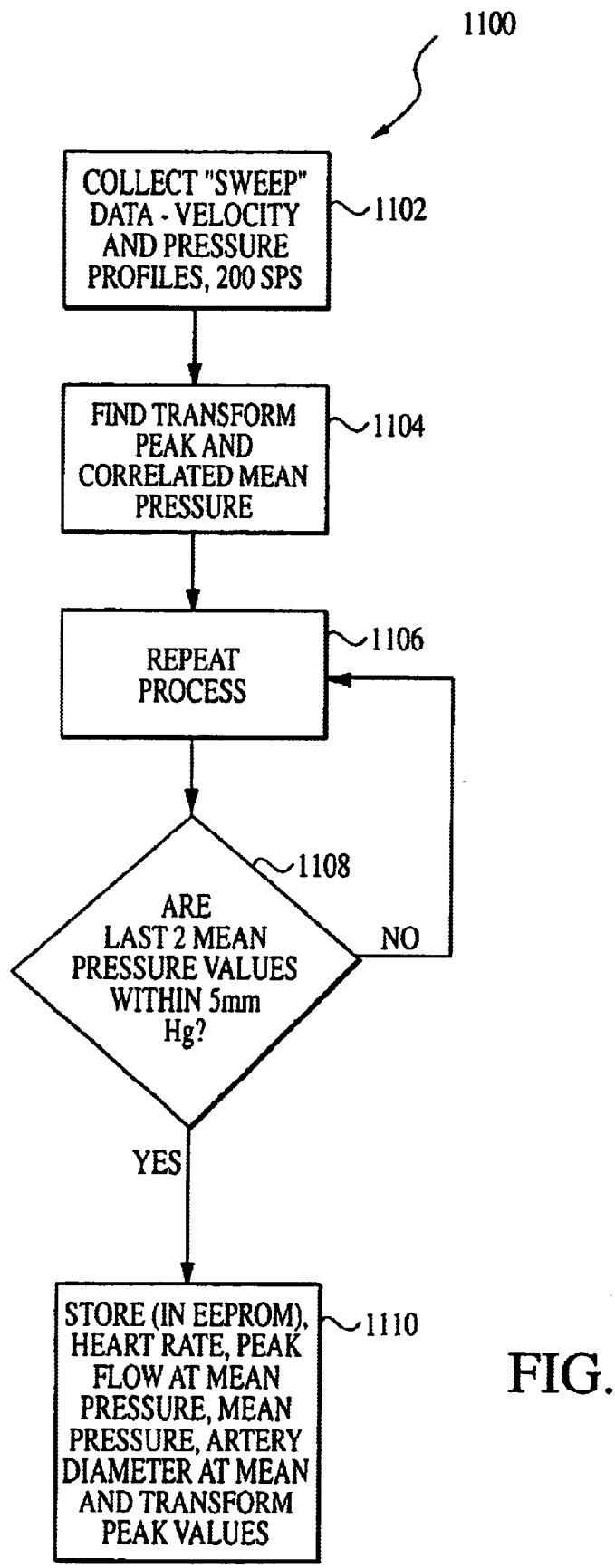
FIG. 11 is a flow diagram illustrating one exemplary embodiment of the method of encoding physiologic parameters within the sensor of the present invention.

Referring now to FIG. 11, a specific exemplary method of encoding physiologic parameters is disclosed. As shown in FIG. 11, the method 1100 comprises collecting pressure and velocity data from a given patient using the sensor 1100 to perform applanation sweeps per step 1102. Next, in step 1104, the data obtained during step 1102 is analyzed using the aforementioned time-frequency or hemodynamic parameter measurement methods as set forth in Applicant's aforementioned copending U.S. patent applications previously incorporated herein, although it will be recognized that other methods of analysis may be substituted. The result of this analysis is an estimate of mean blood pressure within the measured patient. Next, in step 1106, steps 1102 and 1104 are repeated in order to derive a second estimate of the mean blood pressure. In step 1108, the two preceding estimates of mean blood pressure are evaluated to determine if they fall within predetermined acceptance criteria. In the illustrated embodiment, the allowance band of 5 mm Hg (i.e., the last two estimates must be within 5 mm Hg of each other) is used, although other values and in fact other criteria may be substituted. This step 1108 provides reasonable assurance that the sensor is placed correctly on the subject, is being used on the same patient (i.e., the disposable sensor assembly is not being reused on another subject), and the data is not corrupted.

Lastly, in step 1110, the collected data (including for example mean pressure, heart rate, peak blood flow at mean pressure, kinetic energy, arterial diameter at mean pressure, and transform peak values) are stored in the EEPROM or other storage device previously described. This data collectively (or subsets thereof) comprises a characteristic signature for a given sensor assembly and patient.

Figure 12:
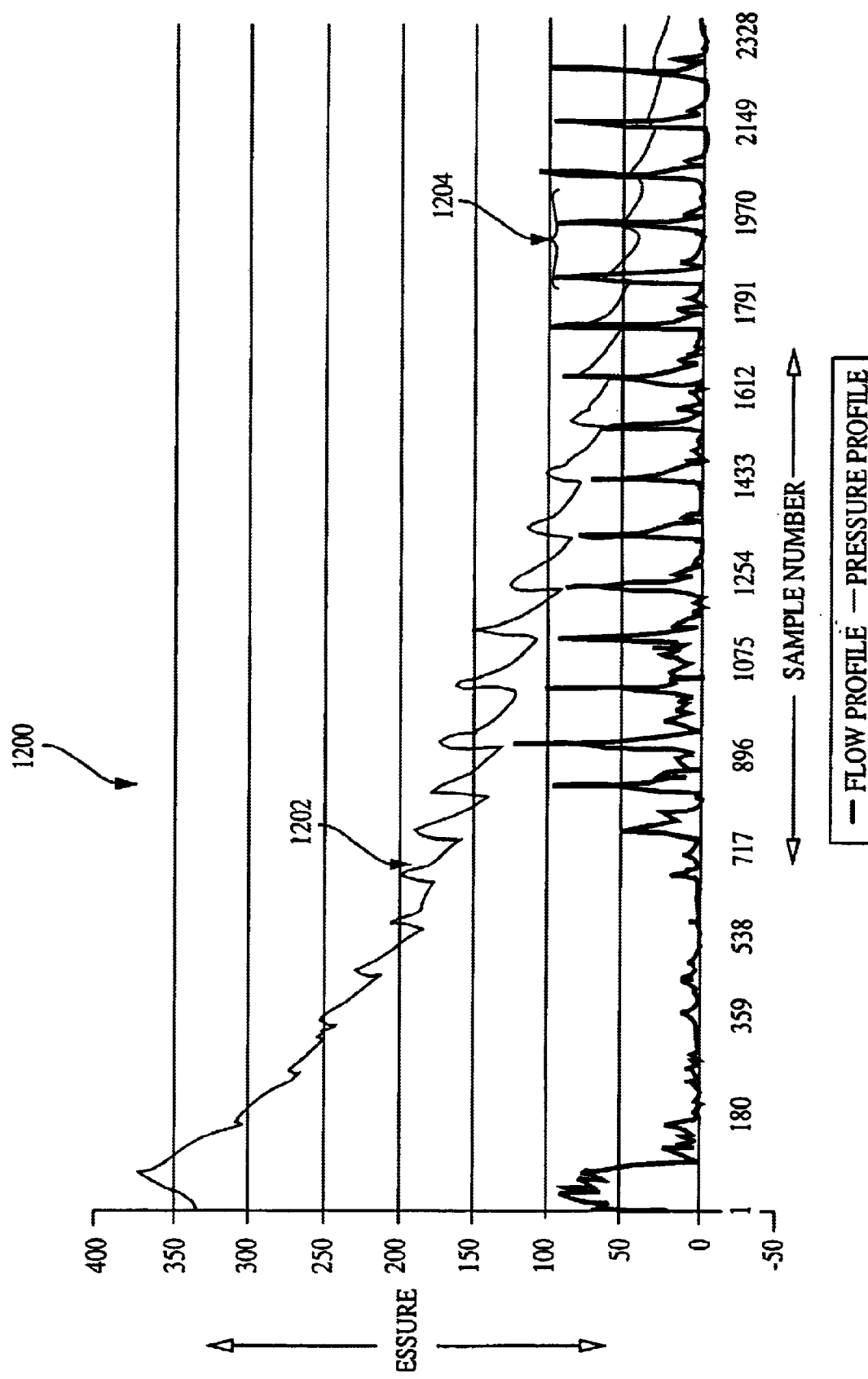
FIG. 12 is an exemplary plot of pressure and arterial blood velocity data which is encoded using the method of the present invention.

Referring now to FIG. 12, an exemplary plot of measured pressure and blood flow/velocity data obtained during a system calibration cycle and which is subsequently encoded using the present invention is described. The plot 1200 illustrates the applanation (pressure) sweep 1202 as a function of the number of samples; note that per the illustrated embodiment, a sampling rate of 200 samples per second is chosen, although other rates or even variable rates may be used. Also illustrated is the blood flow/velocity profile 1204 as a function of the number of samples.

It is noted that many variations of the methods described above may be utilized consistent with the present invention. Specifically, certain steps are optional and may be performed or deleted as desired. Similarly, other steps (such as additional data sampling, processing, filtration, calibration, display, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of calibrating a transducer element, comprising:
    providing a transducer element having a predetermined operating response and an associated storage device, said element adapted to tonometrically measure the pressure associated with a blood vessel;
    determining the bridge voltage $E_b$ and signal output voltage $E_s$ of said pressure transducer under varying conditions of temperature and pressure;
    determining a plurality of calibration parameters based at least in part on said acts of determining voltage;
    storing data representative of said calibration parameters within said storage device; and
    calibrating said transducer element based at least in part on said stored calibration parameters.

2. The method of claim 1, wherein said act of calibrating said transducer element comprises at least periodically calibrating said element during use of said element on a living subject.

3. The method of claim 2, further comprising:
    applying at least one acceptance criterion during said act of calibrating; and
    selectively retaining or discarding, as appropriate, said transducer element and associated storage device based on said act of applying.

4. The method of claim 1, further comprising:
    at least periodically replacing said transducer element and associated storage device, said replacement associated storage device having calibration data which is specifically related to said replacement transducer element; and
    calibrating said transducer element after said act of replacing at least periodically during use.

5. A method of calibrating a transducer element, comprising:
providing a transducer element having a predetermined operating response and an associated storage device, said element adapted to tonometrically measure the pressure associated with a blood vessel;
determining a bridge voltage and signal output voltage of said pressure transducer under varying conditions of temperature and pressure;
determining a plurality of calibration parameters based at least in part on said acts of determining voltage;
storing data representative of said calibration parameters within said storage device; and
calibrating said transducer element based at least in part on said stored calibration parameters.

6. A method of calibrating a transducer element, comprising:
providing a transducer element having a predetermined operating response and an associated storage device, said element adapted to tonometrically measure the pressure associated with a blood vessel;
determining a first voltage and second voltage of said pressure transducer under varying conditions of temperature and pressure;
determining a plurality of calibration parameters based at least in part on said first and second voltages;
storing data representative of said calibration parameters within said storage device; and
calibrating said transducer element based at least in part on said stored calibration parameters.

7. The method of claim 6, wherein said act of calibrating said transducer element comprises at least periodically calibrating said element during use of said element on a living subject.

8. The method of claim 7, further comprising:
applying at least one acceptance criterion during said act of calibrating; and
selectively retaining or discarding, as appropriate, said transducer element and associated storage device based on said act of applying.

9. The method of claim 6, further comprising:
at least periodically replacing said transducer element and associated storage device, said replacement associated storage device having calibration data which is specifically related to said replacement transducer element; and
calibrating said transducer element after said act of replacing at least periodically during use.

10. A method of calibrating a sensor means, comprising:
providing a sensor means having a predetermined operating response and an associated means for storing data, said sensor means adapted to tonometrically measure the pressure associated with a blood vessel;
determining a first voltage and second voltage of said sensor means under varying conditions of temperature and pressure;
determining a plurality of calibration parameters based at least in part on said first and second voltages;
storing data representative of said calibration parameters within said means for storing; and
calibrating said sensor means based at least in part on said stored calibration parameters.

11. A transducer element having a predetermined operating response and an associated storage device, said element adapted to tonometrically measure the pressure associated with a blood vessel, said element being adapted for calibration according to the method comprising;
determining a bridge voltage and output voltage of said pressure transducer under varying conditions of temperature and pressure;
determining a plurality of calibration parameters based at least in part on said bridge and output voltages;
storing data representative of said calibration parameters within said storage device; and
calibrating said transducer element based at least in part on said stored calibration parameters.

12. A transducer element having a predetermined operating response and an associated storage device, said element adapted to tonometrically measure the pressure associated with a blood vessel, said operating response comprising a bridge voltage and output voltage which may each vary with temperature and pressure;
wherein a plurality of calibration parameters for said transducer element are:
(i) determined based at least in part on said bridge and output voltages, and
(ii) stored within said storage device;
said calibration parameters comprising at least in part the basis for calibration of said transducer element.

13. A replaceable component of a medical device, comprising:
at least one pressure transducer element adapted to generate an electrical signal;
a storage device, physically co-located and operatively connected to said at least one pressure transducer element, adapted to store therein a plurality of data related to the calibration of said at least one pressure transducer element and said electrical signal, said data being stored prior to use and retrievable from said storage device subsequent to being stored; and
at least one acoustic transducer adapted to generate an acoustic signal and receive an echo resulting therefrom;
wherein said component is adapted for data communication with a host device for measuring the blood pressure of a living organism based at least in part on said electrical signal and echo.

14. The component of claim 13, wherein said at least one pressure transducer element comprises a silicon strain beam pressure transducer capable of generating an electrical signal in response to pressure applied thereto.

15. The component of claim 13, wherein at least a portion of said data comprises prestored data relating to the compatibility of said pressure transducer with said host device.

16. The component of claim 13, wherein said data is utilized to calibrate said pressure transducer at least periodically during the measurement of said blood pressure.

17. A replaceable component of a medical device, comprising:
at least one pressure sensing means adapted to generate an electrical signal;
means, physically co-located and operatively connected to said at least one pressure sensing means, for storing therein a plurality of data related to the calibration of said at least one pressure sensing means and said electrical signal, said data being stored prior to use and retrievable from said means for storing subsequent to being stored; and
at least one acoustic transducer adapted to generate an acoustic signal and receive an echo resulting therefrom;

wherein said component is adapted for data communication with a means for determining the blood pressure of a living organism based at least in part on said electrical signal and echo.

18. A replaceable component of a medical device, comprising:

at least one pressure transducer element adapted to generate an electrical signal;

a storage device, physically co-located and operatively connected to said at least one pressure transducer element, adapted to store therein a plurality of data related to the calibration of said at least one pressure transducer element and said electrical signal, said data being stored prior to use and retrievable from said storage device subsequent to being stored; and wherein said component is adapted for data communication with (i) at least one acoustic transducer adapted to generate an acoustic signal and receive an echo resulting therefrom, and (ii) a host device for measuring the blood pressure of a living organism based at least in part on said electrical signal and echo.

19. The component of claim 18, wherein said at least one pressure transducer element comprises a silicon strain beam pressure transducer capable of generating an electrical signal in response to pressure applied thereto.

20. The component of claim 18, wherein at least a portion of said data comprises prestored data relating to the compatibility of said pressure transducer with said host device.

21. The component of claim 18, wherein said data is utilized to calibrate said pressure transducer at least periodically during the measurement of said blood pressure.

* * * * *